(12) United States Patent
Jiang et al.

(10) Patent No.: US 8,143,336 B2
(45) Date of Patent: Mar. 27, 2012

(54) ACTIVATED HALO-CONTAINING ARALKYLSILANE COMPOSITION, PROCESS OF PREPARING SAME AND RUBBER COMPOSITIONS MADE THEREFROM

(75) Inventors: Ping Jiang, New City, NY (US); Juan Alfonso, Hopewell Junction, NY (US); Eric R. Pohl, Mount Kisco, NY (US)

(73) Assignee: Momentive Performance Materials Inc., Albany, NY (US)

( * ) Notice: Subject to any disclaimer, the term of this patent is extended or adjusted under 35 U.S.C. 154(b) by 672 days.

(21) Appl. No.: 12/187,765

(22) Filed: Aug. 7, 2008

(65) Prior Publication Data
US 2010/0036018 A1 Feb. 11, 2010

(51) Int. Cl.
*C08K 5/54* (2006.01)
(52) U.S. Cl. ........................................ 524/263; 524/261
(58) Field of Classification Search .................. 524/263, 524/261
See application file for complete search history.

(56) References Cited

U.S. PATENT DOCUMENTS

| | | | |
|---|---|---|---|
| 3,538,137 A | 11/1970 | Viventi | |
| 5,116,886 A | 5/1992 | Wolff et al. | |
| 5,268,439 A | 12/1993 | Hergenrother et al. | |
| 5,821,290 A | 10/1998 | Labauze | |
| 6,005,027 A | 12/1999 | Guillet et al. | |
| 6,384,125 B1 | 5/2002 | Bergstrom et al. | |
| 6,706,398 B1 | 3/2004 | Revis | |
| 7,625,965 B2 * | 12/2009 | Jiang et al. | 524/263 |
| 7,816,435 B2 * | 10/2010 | Jiang et al. | 524/263 |
| 2004/0052939 A1 | 3/2004 | Boswell et al. | |
| 2008/0194746 A1 | 8/2008 | Jiang et al. | |

FOREIGN PATENT DOCUMENTS

| | | |
|---|---|---|
| EP | 0631982 | 1/1995 |
| WO | WO 9311190 | 6/1993 |

OTHER PUBLICATIONS

The BET method of measuring surface area, Journal of the American Chemical Society, vol. 60, p. 309, 1938; Vanderbilt Rubber Handbook, pp. 344-346, 1978.
U.S. Appl. No. 11/981,371, filed Oct. 31, 2007, Jiang, Ping.

* cited by examiner

*Primary Examiner* — Peter D Mulcahy
(74) *Attorney, Agent, or Firm* — Dominick G. Vicari; Joseph S. Ostroff; Wiggin and Dana LLP

(57) ABSTRACT

The invention is directed to an activated halo-containing aralkylsilanes possessing at least one hydrolyzable group bonded to a silicon atom and at least one halo functional group bonded to a carbon atom to which both the silicon atom and an aromatic group are covalently bonded. The invention is also directed to a process for making such a silane as well as its use in rubber compositions and articles containing such rubber compositions, such as tires.

22 Claims, No Drawings

ACTIVATED HALO-CONTAINING ARALKYLSILANE COMPOSITION, PROCESS OF PREPARING SAME AND RUBBER COMPOSITIONS MADE THEREFROM

BACKGROUND OF THE INVENTION

1) Field of the Invention

The present disclosure relates to activated halo-containing aralkylsilanes and their preparation. The disclosure also relates to rubber compositions containing such silanes and articles such as tires made therefrom.

2) Description of Related Art

The use of the silica/silane-filler system to reduce the rolling resistance and improve the wet traction of passenger car tires is well known in the art. A reduction of rolling resistance and therefore less fuel consumption are also of strong interest for truck tires. However, the use of silica to replace carbon black filler in natural rubber (NR) containing formulations, such as truck tread compounds, is limited, due to the poor abrasion resistance. At the present time, truck tire treads use highly reinforcing carbon black for maximum reinforcement and excellent resistance to abrasion. The replacement of carbon black by silica in truck applications has been hampered by ineffective coupling of the silica to the polymer chains of natural rubber.

The polysulfurized alkoxysilanes, such as bis(triethoxysilylpropyl)tetrasulfite (TESPT), and blocked mercapto-functional silanes such as 3-octanoylthio-1-propyltriethoxysilane, are currently regarded as the most effective and the most widely used coupling agents in rubber compositions for tires, especially those compositions containing styrene-butadiene rubber or butadiene rubber. However, the reinforcing efficiency and abrasion resistance of vulcanizates filled with silica and coupled with sulfur-containing silanes are insufficient to justify the replacement of carbon black in formulations containing high levels of natural rubber.

The use of non-sulfur, halo-functional silanes is disclosed in co-pending applications, namely U.S. patent application Ser. Nos. 11/703,969 and 11/981,371. These disclosures are focused on the use of activated double bonds to improve the coupling between fillers and polymer, notably natural rubber. The halo-functional silanes were found to improve the reinforcing index, dynamic properties, such as tan δ at 60° C., and abrasion resistance of silica filled rubber compositions containing high levels of natural rubber. Unfortunately, these halo-functional silanes are not readily available because they rely on the hydrosilylation of halomethylstyrene or its derivatives, intermediates that are difficult to manufacture in high yields and at low costs.

It would be desirable to have halo-containing silanes for use in various rubber and other applications, such as adhesives, sealants, coatings, glass fiber sizings, and filler treatments, and the like. What is needed then are halo-silanes that are more readily manufacturable because they do not employ a halomethylstyrene intermediate in their manufacture. The present invention provides a solution to that need.

BRIEF DESCRIPTION OF THE INVENTION

An embodiment of the invention is directed to an activated halo-containing aralkylsilane possessing at least one hydrolyzable group bonded to a silicon atom and at least one halo functional group bonded to a carbon atom to which both an aromatic group and the silicon atom are covalently bonded.

The halo-containing aralkylsilane of the invention is of the generalized structural Formula (1)

$$X^1X^2X^3Si—C(R^1)_{2-a}(Z^1_a)\text{-}G\text{-}(CR_{3-c}—Z^2_c)_b \quad (1)$$

wherein:

$X^1$ is a hydrolyzable moiety selected from the group consisting of Cl—, Br—, I—, $R^2O$—, $R^2(=O)O$—, $R^2_2C=NO$—, and $R^2_2NO$—, wherein each $R^2$ is independently selected from the group consisting of hydrogen, straight, cyclic or branched alkyl, alkenyl, aryl and aralkyl groups wherein each $R^2$, other than hydrogen, contains from 1 to 18 carbon atoms and optionally at least one heteroatom selected from the group consisting of oxygen and sulfur;

each $X^2$ and $X^3$ is independently selected from $X^1$ and $R^3$ groups wherein each $R^3$ is independently selected from the group consisting of hydrogen, alkyl, alkenyl, aryl and aralkyl groups wherein each $R^3$, other than hydrogen, contains from 1 to 18 carbon atoms and optionally at least one heteroatom selected from the group consisting of oxygen and sulfur;

$R^1$ is selected from the group consisting of hydrogen, alkyl, alkenyl, aryl or aralkyl wherein $R^1$, other than hydrogen, contains from 1 to 10 carbon atoms, and optionally at least one heteroatom selected from the group consisting of oxygen, sulfur, fluorine, chlorine, bromine and iodine;

each occurrence of $Z^1$ and $Z^2$ is independently a halogen atom selected from the group consisting of F—, Cl—, Br— and I—;

G is a monovalent or polyvalent aromatic hydrocarbon group of Formula (2):

$$(-)_{1+b}C_6R^4{}_{5-b} \quad (2)$$

wherein the six carbon atoms are part of an aromatic ring structure and each occurrence of $R^4$ is independently selected from the group consisting of hydrogen, alkyl, alkenyl, aryl and aralkyl groups wherein each $R^4$, other than hydrogen, contains from 1 to 18 carbon atoms;

each occurrence of R is independently selected from the group consisting of hydrogen, alkyl, alkenyl, aryl and aralkyl wherein each R, other than hydrogen, contains from 1 to 30 carbon atoms; and, a, b and c are integers whereby a is 1; b is from 0 to 5; and c is from 1 to 3.

Another embodiment of the invention is directed to a composition comprising: (a) at least one halo-containing aralkylsilane of the structural Formula (1) where a is 1; and (b) at least a silane of the structural Formula (1) where a is 0.

Another embodiment of the invention is directed to a process for preparing a halo-containing aralkylsilane. The process comprises the steps of:

(a) reacting a hydridosilane (i) with a carbon-carbon double bond-containing aralkane (ii) in the presence of an alpha-selective hydrosilylation catalyst (iii) to provide an aralkylsilane (iv);

(b) reacting the reaction product of step (a) with chlorine (v), optionally in the presence of a chlorination catalyst (vi) to yield a halo-containing aralkylsilane;

(c) optionally, reacting the reaction product of step (b) with $X^1$—H (vii), wherein $X^1$ is selected from a hydrolyzable group consisting of Cl—, Br—, I—, $R^2O$—, $R^2(=O)$O—, $R^2_2C=NO$—, and $R^2_2NO$—, wherein each $R^2$ is independently selected from the group consisting of hydrogen, straight, cyclic or branched alkyl, alkenyl, aryl and aralkyl groups wherein each $R^2$, other than hydrogen, contains from 1 to 18 carbon atoms and optionally at least one heteroatom selected from the group consisting of oxygen and sulfur.

Yet another embodiment of the invention is directed to a rubber composition comprising:
(a) at least one rubber component;
(b) at least one filler;
(c) optionally, at least one activating agent; and,
(d) a halo-containing aralkylsilane of Formula (1). In an embodiment, the filler (b) is silane-reactive.

The halo-containing aralkylsilanes of the invention provide improved properties to rubber compositions used in cured articles, such as the non-limiting example of tires. In addition, these silanes can be made in high yields by a process involving the direct chlorination of an aralkylsilane.

DETAILED DESCRIPTION OF THE INVENTION

It will be understood that all weight percents are based upon total weight percent of the rubber composition herein, unless stated otherwise.

It will also be understood that any numerical range recited herein includes all subranges within that range and can further include any combination of the various endpoints of such ranges and/or subranges.

In one embodiment of the invention, there is provided a halo-containing aralkylsilane possessing at least one hydrolyzable group bonded to a silicon atom and at least one halo functional group bonded to a carbon atom to which both an aromatic group and the silicon atom are covalently bonded.

The halo-containing aralkylsilane is of the generalized structural Formula (1)

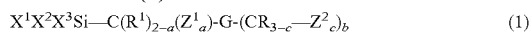

wherein:

$X^1$ is a hydrolyzable moiety selected from the group consisting of Cl—, Br—, I—, $R^2O$—, $R^2(=O)O$—, $R^2_2C=NO$—, and $R^2_2NO$—, wherein each $R^2$ is independently selected from the group consisting of hydrogen, straight, cyclic or branched alkyl, alkenyl, aryl and aralkyl groups wherein each $R^2$, other than hydrogen, contains from 1 to 18 carbon atoms and optionally at least one heteroatom selected from the group consisting of oxygen and sulfur;

each $X^2$ and $X^3$ is independently selected from $X^1$ and $R^3$ groups wherein each $R^3$ is independently selected from the group consisting of hydrogen, alkyl, alkenyl, aryl and aralkyl groups wherein each $R^3$, other than hydrogen, contains from 1 to 18 carbon atoms and optionally at least one heteroatom selected from the group consisting of oxygen and sulfur;

$R^1$ is selected from the group consisting of hydrogen, alkyl, alkenyl, aryl and aralkyl wherein $R^1$, other than hydrogen, contains from 1 to 10 carbon atoms, and optionally at least one heteroatom selected from the group consisting of oxygen, sulfur, fluorine, chlorine, bromine and iodine;

each occurrence of $Z^1$ and $Z^2$ is independently a halogen atom selected from the group consisting of F—, Cl—, Br— and I—;

G is a monovalent or polyvalent aromatic hydrocarbon group of Formula (2):

wherein the six carbon atoms are part of an aromatic ring structure and each occurrence of $R^4$ is independently selected from the group consisting of hydrogen, alkyl, alkenyl, aryl and aralkyl groups wherein each $R^4$, other than hydrogen, contains from 1 to 18 carbon atoms;

each occurrence of R is independently selected from the group consisting of hydrogen, alkyl, alkenyl, aryl and aralkyl wherein each R, other than hydrogen, contains from 1 to 30 carbon atoms; and, a, b and c are integers whereby a is 1; b is from 0 to 5; and c is from 1 to 3.

In connection with the silane of Formula (1), "alkyl" includes straight, branched and cyclic alkyl groups; "alkenyl' includes any straight, branched, or cyclic alkenyl group containing one or more carbon-carbon double bonds, where the point of substitution can be either at a carbon-carbon double bond or elsewhere in the group; "alkynyl" includes any straight, branched or cyclic alkynyl group containing one or more carbon-carbon triple bonds, where the point of substitution can be either at a carbon-carbon triple bond or elsewhere in the group; "aryl" includes the non-limiting group of any aromatic hydrocarbon from which one hydrogen atom has been removed; "aralkyl" includes, but is not limited to, any of the aforementioned alkyl groups in which one or more hydrogen atoms have been substituted by the same number of like and/or different aryl (as defined herein) substituents. Specific and non-limiting examples of alkyls include, but are not limited to, methyl, ethyl, propyl and isobutyl. Specific and non-limiting examples of alkenyls include, but are not limited to, vinyl, propenyl, allyl, methallyl, ethylidenyl norbornane, ethylidene norbornyl and ethylidene norornenyl. Specific and non-limiting examples of aryls include, but are not limited to, tolyl, xylyl, phenyl and naphthalenyl. Specific and non-limiting examples of aralkyls include, but are not limited to, benzyl and phenethyl.

$X^1$ of the general Formula (1) is a hydrolyzable group. Some non-limiting representative examples of $X^1$ include alkoxy groups such as the non-limited examples methoxy, ethoxy, propoxy, isopropoxy, butoxy, phenoxy and benzyloxy; hydroxyl group; halo groups such as the non-limiting examples chloro, bromo and iodo; oximato groups such as the non-limiting examples methylethyloximato, phenylmethyloximato and dimethyloximato; amineoxy groups such as the non-limiting examples dimethylamineoxy, diethylamineoxy and methylphenyamineoxy; and, acyloxy groups such as the non-limiting examples formyloxy, acetoxy and propanoyloxy.

Some representative non-limiting examples of $X^2$ and $X^3$ in Formula (1) include the representative examples listed above for $X^1$ as well as hydrogen, alkyl groups such as the non-limiting examples methyl, ethyl, propyl, isopropyl, sec-butyl and cyclohexyl; higher straight-chain alkyl such as butyl, hexyl, octyl, lauryl and octadecyl; alkenyl groups such as the non-limiting examples vinyl, allyl, methallyl and 3-butenyl; aryl groups such as the non-limiting examples phenyl and tolyl; and, aralkyl groups such as the non-limiting examples benzyl and phenethyl.

Each $Z^1$ and $Z^2$ of Formula (1) can independently be halogen atoms, F—, Cl—, Br— and I—. In an embodiment, both $Z^1$ and $Z^2$ are halogen atom Cl—.

R of Formula (1) can be hydrogen; a straight, branched or cyclic alkyl group of preferably up to 30 carbon atoms, more preferably up to 10 carbon atoms, even more preferably up to 6 carbon atoms and most preferably 3 carbon atoms; a straight, branched or cyclic alkenyl group containing one or more carbon-carbon double bond where the point of substitution can be either at a carbon-carbon double bond or elsewhere in the group and where the alkenyl group contains preferably up to 30 carbon atoms, more preferably up to 10 carbon atoms, even more preferably up to 6 carbon atoms and most preferably up to 3 carbon atoms; or an aryl group containing preferably up to 30 carbon atoms, more preferably up to 20 carbon atoms, even more preferably up to 12 carbon atoms and most preferably up to 8 carbon atoms.

Representative and non-limiting examples of R include alkyl groups such as the non-limiting examples methyl, ethyl, propyl and isobutyl; alkenyl groups such as the non-limiting examples vinyl, propenyl, allyl, methallyl, ethylidenyl norbornane, ethylidene norbornyl, ethylidenyl norbornene and ethylidene norbornenyl; aryl groups such as the non-limiting examples phenyl and naphthalenyl; and, aralkyl groups such as the non-limiting examples benzyl and phenethyl. Some representative examples of "cyclic alkyl" and "cyclic alkenyl" include, but are not limited to, norbornyl, norbornenyl, ethylnorbornyl, ethylnorbornenyl, ethylcyclohexyl, ethylcyclohexenyl, cyclohexylcyclohexyl and cyclododecatrienyl.

$R^1$ of Formula (1) can be hydrogen; a straight, branched or cyclic alkyl group of preferably up to 10 carbon atoms and optionally at least one heteroatom selected form the group consisting of oxygen, sulfur, fluorine, chlorine, bromine and iodine, more preferably up to 6 carbon atoms, even more preferably up to 3 carbon atoms and most preferably 1 carbon atom; a straight, branched or cyclic alkenyl group containing one or more carbon-carbon double bond where the point of substitution can be either at a carbon-carbon double bond or elsewhere in the group and where the alkenyl group contains preferably up to 10 carbon atoms, more preferably up to 6 carbon atoms, and even more preferably up to 3 carbon atoms; or an aryl group containing preferably up to 10 carbon atoms, and more preferably up to 8 carbon atoms, and even more preferably 6 carbon atoms.

Representative and non-limiting examples of $R^1$ include alkyl groups such as the non-limiting examples methyl, ethyl, propyl, 3-chloropropyl, 3-oxabutyl, 2- and isobutyl; alkenyl groups such as the non-limiting examples vinyl, propenyl, allyl, methallyl, ethylidenyl norbornane, ethylidene norbornyl, ethylidenyl norbornene and ethylidene norbornenyl; aryl groups such as the non-limiting examples phenyl and naphthalenyl; and, aralkyl groups such as the non-limiting examples benzyl and phenethyl. Some representative examples of "cyclic alkyl" and "cyclic alkenyl" include, but are not limited to, norbornyl, norbornenyl, ethylnorbornyl, ethylnorbornenyl, ethylcyclohexyl, ethylcyclohexenyl, and cyclohexyl.

$R^2$ of Formula (1) can be hydrogen; a straight, branched or cyclic alkyl group of preferably up to 18 carbon atoms, more preferably up to 10 carbon atoms, even more preferably up to 3 carbon atoms and most preferably 2 carbon atom; a straight, branched or cyclic alkenyl group containing one or more carbon-carbon double bond where the point of substitution can be either at a carbon-carbon double bond or elsewhere in the group and where the alkenyl group contains preferably up to 18 carbon atoms, more preferably up to 6 carbon atoms, and even more preferably up to 3 carbon atoms; an aryl group containing preferably up to 10 carbon atoms, and more preferably up to 8 carbon atoms, and even more preferably 6 carbon atoms.

Representative and non-limiting examples of $R^2$ include alkyl groups such as the non-limiting examples methyl, ethyl, propyl and isobutyl; alkenyl groups such as the non-limiting examples vinyl, propenyl, allyl, methallyl, ethylidenyl norbornane, ethylidene norbornyl, ethylidenyl norbornene and ethylidene norbornenyl; aryl groups such as the non-limiting examples phenyl and naphthalenyl; and, aralkyl groups such as the non-limiting examples benzyl and phenethyl. Some representative examples of "cyclic alkyl" and "cyclic alkenyl" include, but are not limited to, norbornyl, norbornenyl, ethylnorbornyl, ethylnorbornenyl, ethylcyclohexyl, ethylcyclohexenyl, and cyclohexyl.

$R^3$ of Formula (1) can be hydrogen; a straight, branched or cyclic alkyl group of preferably up to 18 carbon atoms, more preferably up to 10 carbon atoms, even more preferably up to 3 carbon atoms and most preferably 1 carbon atom; a straight, branched or cyclic alkenyl group containing one or more carbon-carbon double bond where the point of substitution can be either at a carbon-carbon double bond or elsewhere in the group and where the alkenyl group contains preferably up to 18 carbon atoms, more preferably up to 6 carbon atoms, and even more preferably up to 3 carbon atoms; or an aryl group containing preferably up to 10 carbon atoms, and more preferably up to 8 carbon atoms, and even more preferably 6 carbon atoms.

Representative and non-limiting examples of $R^3$ include alkyl groups such as the non-limiting examples methyl, ethyl, propyl and isobutyl; alkenyl groups such as the non-limiting examples vinyl, propenyl, allyl, methallyl, ethylidenyl norbornane, ethylidene norbornyl, ethylidenyl norbornene and ethylidene norbornenyl; aryl groups such as the non-limiting examples phenyl and naphthalenyl; and, aralkyl groups such as the non-limiting examples benzyl and phenethyl. Some representative examples of "cyclic alkyl" and "cyclic alkenyl" include, but are not limited to, norbornyl, norbornenyl, ethylnorbornyl, ethylnorbornenyl, ethylcyclohexyl, ethylcyclohexenyl, and cyclohexyl.

$R^4$ of Formula (1) can be hydrogen; a straight, branched or cyclic alkyl group of preferably up to 18 carbon atoms, more preferably up to 10 carbon atoms, even more preferably up to 3 carbon atoms and most preferably 2 carbon atom; a straight, branched or cyclic alkenyl group containing one or more carbon-carbon double bond where the point of substitution can be either at a carbon-carbon double bond or elsewhere in the group and where the alkenyl group contains preferably up to 18 carbon atoms, more preferably up to 6 carbon atoms, and even more preferably up to 3 carbon atoms; or an aryl group containing preferably up to 10 carbon atoms, and more preferably up to 8 carbon atoms, and even more preferably 6 carbon atoms.

Representative and non-limiting examples of $R^4$ include alkyl groups such as the non-limiting examples methyl, ethyl, propyl and isobutyl; alkenyl groups such as the non-limiting examples vinyl, propenyl, allyl, methallyl, ethylidenyl norbornane, ethylidene norbornyl, ethylidenyl norbornene and ethylidene norbornenyl; aryl groups such as the non-limiting examples phenyl and naphthalenyl; and, aralkyl groups such as the non-limiting examples benzyl and phenethyl. Some representative examples of "cyclic alkyl" and "cyclic alkenyl" include, but are not limited to, norbornyl, norbornenyl, ethylnorbornyl, ethylnorbornenyl, ethylcyclohexyl, ethylcyclohexenyl, and cyclohexyl.

G is a monovalent, divalent or polyvalent aromatic group containing six carbon atoms arranged in a ring structure and b+1 valences. Representative examples of G include 1,4-phenylenyl, 1,3-phenylenyl, 1,2-phenylenyl, 3-methyl-1,4-phenylenyl, 2-methyl-1,4-phenylenyl, 2,3,5-trimethyl-1,4-phenylenyl, 3-butyl-1,4-phenylenyl and 3-ethyl-1,4-phenylenyl.

In an embodiment, the halo-containing aralkylsilane is of Formula (1) wherein $R^1$ is methyl, ethyl or propyl; $R^2$ is methyl, ethyl or propyl, and more preferably ethyl; $R^3$ is methyl; $R^4$ is hydrogen or methyl; $X^1$ is ethoxy; $X^2$ and $X^3$ is ethoxy or methyl, and more preferably ethoxy; a is 1; b is 0 or 1 and c is 1 to 3. Illustratively, in the activated halo-containing aralkylsilane of Formula (1), a is 1, b is 1 and c is 1.

Representative and non-limiting examples of the activated halo-containing aralkylsilane include [1-chloro-1-(4-chloromethyl-phenyl)-ethyl]-diethoxy-methyl-silane, [1-chloro-1-(4-chloromethyl-phenyl)-ethyl]-triethoxy-silane, [1-chloro-1-(4-chloromethyl-phenyl)-ethyl]-ethoxy-dimethyl-silane, [1-bromo-1-(4-bromomethyl-phenyl)-ethyl]-diethoxy-methyl-silane, [1-bromo-1-(4-bromomethyl-phenyl)-ethyl]-triethoxy-silane, [1-Chloro-1-(4-methyl-phenyl)-ethyl]-diethoxy-methyl-silane, [1-chloro-1-(4-methyl-phenyl)-ethyl]-triethoxy-silane, [1-chloro-1-(4-chloromethyl-phenyl)-propyl]-diethoxy-methyl-silane, {1-chloro-1-[4-(1-chloro-ethyl)-phenyl]-propyl}-triethoxy-silane, [1-chloro-1-(4-dichloromethyl-phenyl)-propyl]-diethoxy-methyl-silane, [1-chloro-1-(4-dichloromethyl-phenyl)-propyl]-triethoxy-silane, [1-chloro-1-(4-trichloromethyl-phenyl)-propyl]-diethoxy-methyl-silane, [1-chloro-1-(4-trichloromethyl-phenyl)-propyl]-triethoxy-silane, [1-chloro-1-(4-chloromethyl-phenyl)-ethyl]-trimethoxy-silane, [1-chloro-1-(4-chloromethyl-phenyl)-ethyl]-tripropoxy-silane, and chloro-[1-chloro-1-(4-chloromethyl-phenyl)-propyl]-dimethyl-silane.

Mixtures of halo-containing aralkysilanes according to the invention are useful as an additive to filled elastomers (for example, rubber), coatings, adhesives, sealants, glass fiber sizing, and the like. The mixtures result from the halogenation occurring to different locations on the aralkylsilane intermediate, i.e. when a is 1 and b is 0, or a is 0 and b is 1, and when halogenation occurs more than once, i.e. when a is 1, c is 1 to 3, and b is 1 to 5. These mixtures can be advantageous because the halo-containing aralkylsilane has more than one activated halo functional group.

In an embodiment of the invention, there is provided a composition comprising: (a) at least one activated halo-containing aralkyl silane of Formula I wherein a is 1; and (b) at least one activated halo-containing silane of Formula I wherein a is 0.

Another embodiment of the invention is directed to partial hydrolyzates of the halo-containing aralkyl silane. These hydrolyzates occur when the activated halo-containing aralkylsilane is exposed to atmospheric moisture. A partial hydrolyzate results when moisture reacts with the hydrolyzable $X^1$—Si group to the extent of not more than 50 mole percent, more preferably, not more than 20 mole percent, and most preferably, not more than 5 mole percent of the total molar amounts of $X^1$—Si group to form SiOH or Si—O—Si bonds. The reaction may occur due to exposure of the activated halo-containing aralkylsilane to ambient moisture during production and/or storage or as a result of purposefully adding water to cause the hydrolysis and condensation reactions to occur.

Another embodiment of the invention is directed to a process for preparing a halo-containing aralkylsilane. The process comprises the steps of:

(a) reacting a hydridosilane (i) of general Formula (3):

$$HSiX^4X^5X^6 \quad (3)$$

wherein $X^4$ is selected from a hydrolyzable group consisting of F—, Cl—, Br— and I—; each $X^5$ and $X^6$ is independently selected from $X^4$ and $R^3$ groups wherein each $R^3$ is independently selected from the group consisting of hydrogen, alkyl, alkenyl, aryl and aralkyl groups wherein each $R^3$, other than hydrogen, contains from 1 to 18 carbon atoms and optionally at least one heteroatom selected from the group consisting of oxygen and sulfur;

with a carbon-carbon double bond-containing aralkane (ii) of Formula (4):

$$R^5R^6C=C(R^1)-C_6R^4{}_{5-b}(CR_3)_b \quad (4)$$

wherein each occurrence of R is independently selected from the group consisting of hydrogen, alkyl, alkenyl, aryl or aralkyl wherein each R, other than hydrogen, contains from 1 to 30 carbon atoms; $R^1$ is selected from the group consisting of hydrogen, alkyl, alkenyl, aryl or aralkyl wherein $R^1$, other than hydrogen, contains from 1 to 10 carbon atoms; each occurrence of $R^4$ is independently selected from the group consisting of hydrogen, alkyl, alkenyl, aryl and aralkyl groups wherein each $R^4$, other than hydrogen, contains from 1 to 18 carbon atoms; each $R^5$ and $R^6$ is independently selected from the group consisting of hydrogen, alkyl, alkenyl, aryl or aralkyl wherein each $R^5$ and $R^6$, other than hydrogen, contains from 1 to 9 carbon atoms; and the b is an integer of from 0 to 5;

in the presence of an effective amount of an alpha-selective hydrosilylation catalyst (iii) to provide an aralkylsilane of Formula (5):

$$X^4X^5X^6Si-C(R^1)_2-C_6R^4{}_{5-b}-(CR_3)_b \quad (5)$$

(b) reacting the reaction product of step (a) with halogen (iv), optionally in the presence of an effective amount of halogenation catalyst (v) to yield a halo-containing aralkylsilane of Formula (6):

$$X^4X^5X^6Si-C(R^1)_{2-a}(Z^1{}_a)-G-(CR_{3-c}-Z^2{}_c)_b \quad (6)$$

wherein:

each occurrence of $Z^1$ and $Z^2$ is independently a halogen atom selected from the group consisting of F—, Cl—, Br— and I—;

G is a monovalent or polyvalent aromatic hydrocarbon group of Formula (2):

$$(-)_{1+b}C_6R_{5-b} \quad (2)$$

wherein the six carbon atoms are part of an aromatic ring structure and each occurrence of $R^4$ is independently selected from the group consisting of hydrogen, alkyl, alkenyl, aryl and aralkyl groups wherein each $R^4$, other than hydrogen, contains from 1 to 18 carbon atoms; and, a and c are integers given by a is 0 or 1; b is from 0 to 5, and c is from 1 to 3, with the proviso that a+b is equal to or greater than 1; and, (c) optionally, reacting the halo-containing aralkylsilane of step (b) with $X^1$—H, wherein $X^1$ is selected from a hydrolyzable group consisting of Cl—, Br—, I—, $R^2O$—, $R^2(=O)O$—, $R^2{}_2C=NO$—, and $R^2{}_2NO$—, wherein each $R^2$ is independently selected from the group consisting of hydrogen, straight, cyclic or branched alkyl, alkenyl, aryl and aralkyl groups wherein each $R^2$, other than hydrogen, contains from 1 to 18 carbon atoms and optionally at least one heteroatom selected from the group consisting of oxygen and sulfur;

to provide for a halo-containing aralkylsilane of Formula (1).

In another embodiment, the halo-containing aralkylsilane can be made by a process comprising the steps of:

(a) reacting a halo-containing aralkane compound of Formula (7):

$$ZCR^1{}_2-C_6R^4{}_{5-b}(CR_3)_b \quad (7)$$

wherein each occurrence of R is independently selected from the group consisting of hydrogen, alkyl, alkenyl, aryl and aralkyl, wherein each R, other than hydrogen, contains from 1 to 30 carbon atoms; each occurrence of $R^1$ is independently selected from the group consisting of hydrogen, alkyl, alkenyl, aryl and aralkyl wherein each $R^1$, other than hydrogen, contains from 1 to 10 carbon atoms; each occurrence of $R^4$ is independently selected from the group consisting of hydrogen, alkyl, alkenyl, aryl and aralkyl groups wherein each $R^4$, other than hydrogen, contains from 1 to 18 carbon atoms; Z is a halogen selected from the group consisting of chlorine, bromine and iodine; and b is an integer of from 0 to 5;

with an active metal M selected form the group consisting of magnesium, calcium, titanium, iron, cobalt, nickel and zinc, optionally in the presence of a solvent, to provide for a compound of Formula (8):

$$ZMCR^1{}_2\text{—}C_6R^4{}_{5-b}(CR_3)_b \qquad (8)$$

(b) reacting the reaction product of step (a) with a hydridosilane (i) of general Formula (3):

$$HSiX^4X^5X^6 \qquad (3)$$

wherein $X^4$ is a hydrolyzable moiety selected from the group consisting of F—, Cl—, Br— and I—; each $X^5$ and $X^6$ is independently selected from $X^4$ and $R^3$ groups wherein each $R^3$ is independently selected from the group consisting of hydrogen, alkyl, alkenyl, aryl and aralkyl groups wherein each $R^3$, other than hydrogen, contains from 1 to 18 carbon atoms and optionally at least one heteroatom selected from the group consisting of oxygen and sulfur;

to provide an aralkylsilane of Formula (5):

$$X^4X^5X^6Si\text{—}CR^1{}_2\text{—}C_6R^4{}_{5-b}\text{—}(CR_3)_b \qquad (5)$$

(c) reacting the reaction product of step (b) with halogen (iv), optionally in the presence of an effective amount of halogenation catalyst (v) to yield a halo-containing aralkylsilane of Formula (6):

$$X^4X^5X^6Si\text{—}C(R^1)_{2-a}(Z^1{}_a)\text{-G-}(CR_{3-c}\text{—}Z^2{}_c)_b \qquad (6)$$

wherein:
each occurrence of $Z^1$ and $Z^2$ is independently a halogen atom selected from the group consisting of F—, Cl—, Br— and I—;
G is a monovalent or polyvalent aromatic hydrocarbon group of Formula (2):

$$(-)_{1+b}C_6R^4{}_{5-b} \qquad (2)$$

wherein the six carbon atoms are part of an aromatic ring structure and each occurrence of $R^4$ is independently selected from the group consisting of hydrogen, alkyl, alkenyl, aryl and aralkyl groups wherein each $R^4$, other than hydrogen, contains from 1 to 18 carbon atoms; and,
a, b and c are integers whereby a is 0 or 1; b is from 0 to 5, and c is from 1 to 3, with the proviso that a+b is equal to or greater than 1; and,
(d) optionally, reacting the halo-containing aralkylsilane of step (c) with
$X^1$—H, wherein $X^1$ is a hydrolyzable moiety selected from the group consisting of Cl—, Br—, I—, $R^2O$—, $R^2(\!\!=\!\!O)O$—, $R^2{}_2C\!\!=\!\!NO$—, and $R^2{}_2NO$—, wherein each $R^2$ is independently selected from the group consisting of hydrogen, straight, cyclic or branched alkyl, alkenyl, aryl and aralkyl groups wherein each $R^2$, other than hydrogen, contains from 1 to 18 carbon atoms and optionally at least one heteroatom selected from the group consisting of oxygen and sulfur;
to provide for an aralkylsilane of Formula (1). This process is especially useful when $R^1$ is hydrogen.

Representative and non-limiting examples of hydridosilane (i) include trichlorosilane, methyldichlorosilane, dimethylchlorosilane, tribromosilane, methyldibromosilane, fluorodimethylsilane, ethyldichlorosilane, phenyldichlorosilane and isopropyldichlorosilane.

Representative and non-limiting examples of carbon-carbon double bond-containing aralkane (ii) include 1-methyl-4-vinyl-benzene, 1,2-dimethyl-4-vinyl-benzene, 1-isopropenyl-4-methyl-benzene, 1-methyl-4-propenyl-benzene, 1-ethyl-4-(1-methyl-propenyl)-benzene, 1-methyl-2-vinyl-benzene, 2,4-dimethyl-1-vinyl-benzene and 1-methyl-4-styryl-benzene.

The alpha-selective hydrosilylation catalyst (iii) is a catalyst that promotes the addition of the silyl group to the carbon atom that is part of the carbon-carbon double bond group and bonded to the $(-)_{1+b}C_6R^4{}_{5-b}$, referred to as the alpha carbon, and the hydrogen to the other carbon atom that is part of the carbon-carbon double bond group, referred to as the beta carbon. An alpha-selective hydrosilylation catalyst (iii) promotes the addition of the hydridosilane to the alpha carbon in preference to the beta carbon. Preferably the ratio of the silyl group bonded to the alpha carbon to the silyl group bonded to the beta carbon is between 1.1:1 and 1:0, more preferably between 10:1 and 1:0 and most preferably between 20:1 and 1:0.

Alpha-selective hydrosilylation catalyst (iii) include metal complexes and can be either heterogeneous or homogenous. A list of hydrosilylation catalysts is provided in "Comprehensive Handbook on Hydrosilylation" edited by B. Marciniec, (Pergamon Press, Oxford) 1992, the entire contents included by reference. Preferred alpha-selective hydrosilylation catalysts (iii) are complexes of palladium. Palladium catalyzed hydrosilylation of styrene derivatives usually proceeds with high regioselectivity to produce the a isomer or 1-aryl-1-silylethanes, due to the participation of π-benzylic palladium intermediates, as disclosed in Chapter 25 of "The Chemistry of Organic Silicon Compounds," authored by Ojima I., edited by Patai S and Rappoport Z. (John Wiley, Chichester), 1989, the entire contents included by reference.

Representative non-limiting examples of catalyst (iii) include allylpalladium (II) chloride dimer, allylpalladium (II) trifloroacetate dimer, dichlorobis(aceonitrile)palladium (II), dichlorobis(benzonitrile)palladium (II), dichloro(cyloocta1,5-diene)palladium (II), diacetatobis(triphenylphosphine)palladium (II), dibromobis(triphenylphosphine)palladium(II), dicyanobis(triphenylphosphine)palladium(II), dichloro[bis(1,2-diphenylphosphino)ethane]palladium (II), dichlorobis(tricyclohexylphosphine)palladium(II), dichlorobis(triethylphosphine)palladium(II), dichlorobis(triphenylphosphine)palladium(II), diiodobis(triphenylphosphine) palladium(II), benzylchlorobis(triphenylphosphine) palladium(II), benzylbromobis(triphenylphosphine) palladium(II), benzyliodobis(triphenylphosphine)palladium (II), and (chlorophenyl)chlorobis(triphenylphosphine) palladium(II).

The effective amount of alpha-selective hydrosilylation catalyst (iii) is from about 0.001 weight percent to 2 weight percent catalyst (iii), based up the weight of the carbon-carbon double bond-containing aralkane (ii), preferably from about 0.01 weight percent to 1 weight percent catalyst to catalyst (iii), based upon the weight of the carbon-carbon double bond-containing aralkane (ii), and more preferably from about 0.1 weight percent to 0.5 weight percent catalyst to catalyst (iii), based upon the weight of the carbon-carbon double bond-containing aralkane. Preferably, the alpha-selective hydrosilylation catalyst (iii) is added to the carbon-carbon double bond-containing aralkane (ii) and then the hydridosilane (i) is added to this mixture. The alpha-selective hydrosilylation catalyst (iii) can be added all at once or in portions during the course of the reaction.

The hydrosilylation reaction can be carried out at room temperature or at elevated temperatures and at sub-atomospheric, atmospheric or supra-atmospheric pressures. The preferred temperature range is from room temperature (about 20° C.) to 250° C., more preferred from 60° C. to 180° C., and more preferably from 70 to 130° C. The preferred pressure is from atmospheric to 50 mega-Pascal and more preferably from atmospheric to 10 mega-Pascal. The reactions can be carried out in the absence or presence of aprotic solvent, such as, for example, alkanes, aromatic solvents, halogenated solvents, ethers, esters, and the like. Representative solvents include hexane, cyclohexane, benzene, toluene, xylene, naphtha, tetrahydrofuran, dimethoxyethane, ethyl acetate and the like.

Useful halogens (iv) include fluorine, chlorine, bromine and iodine. Illustratively, chlorine is the halogen used. The amount of halogen depends upon the desired amount of halogenation. The amount of reactant can range from about 0.5 mole to about 10 moles of halogen per mole of aralkylsilane, preferably from about 1.0 to about 3 moles of halogen per mole of aralkylsilane, and most preferably from about 1.1 moles to 2.0 moles halogen per mole of aralkylsilane. The reactions can be run at sub-atmospheric, atmospheric or supra-atmospheric pressures and temperature ranging from −40° C. to 200° C., preferably from 20° C. to 100° C. and most preferably from 30° C. to 60° C. Typically, the reactions are carried out in the absence of a solvent. However, if desired, the solvent should be inert the reactions of halogen, such as, for example, halogenated solvents, aromatic solvents, and the like.

The halogenation catalyst (v) promotes the reaction of the halogen with the aralkylsilane by catalyzing the hydrogen abstraction from the alpha-carbon containing the silyl group and/or the alpha carbon of the $-CR_3$ group wherein at least one R is hydrogen, thereby allowing the further reaction to chemically bond a halogen to these positions. The halogenation catalyst (v) should not promote the chlorination of the aromatic ring, which can occur if the catalyst is a strong Lewis acid. Typical halogenation catalysts (v) are peroxides and halides of phosphorus. The amount of halogenation catalyst (v) is from about 0.01 weight percent to about 10 weight percent, based upon the weight of the aralkylsilane intermediate, preferably from about 0.1 weight percent to about 5 weight percent, based upon the weight of the aralkylsilane intermediate, and most preferably from 1 weight percent to about 3 weight percent, based upon the weight of the aralkylsilane intermediate.

Representative non-limiting examples of halogenation catalyst (v) include di(2,4-dichlorobenzoyl)peroxide, tert-butyl peroxypivalate, dilauroyl peroxide, dibenzoyl peroxide, tert-butyl peroxy-2-ethylhexanoate, 1,1-di(tert-butylperoxy)-3,3,5-trimethylcyclohexane, di(tert-butylperoxy)cyclohexane, tert-butyl peroxy-3,5,5-trimethylhexanoate, tert-butyl peroxyacetate, tert-butyl peroxybenzoate, di-tert-amyl peroxide, dicumyl peroxide, di(tert-butylperoxyisopropyl)benzene, 2,5-dimethyl-2,5-di(tert-butylperoxy)hexane, tert-butyl peroxyacetate, tert-butyl peroxybenzoate, di-tert-amyl peroxide, dicumyl peroxide, di(tert-butyl-peroxyisopropyl)benzene, 2,5-dimethyl-2,5-di(tert-butylperoxy)hexane, tert-butyl cumyl peroxide, 2,5-dimethyl-2,5-di(tert-butylperoxy)hexyne-3 and di-tert-butyl peroxide, phosphorus pentachloride, phosorus trichloride and the like. Preferred halogenation catalyst (v) include phosphorus pentachloride and phosorus trichloride.

The activated halo-containing aralkylsilane of step (b) can be further reacted with $X^1$—H compounds. The reaction is referred to as an esterification reaction. The reaction is desirable because it converts the activated halo-containing aralkylsilane of step (b), which contains $-SiX^4X^5X^6$ groups to an activated halo-containing aralkylsilane which contains $-SiX^1X^2X^3$. When the activated halo-containing aralkylsilane of step (b) is exposed to moisture, it generates $X^4$—H, which is poisonous and corrosive. The preferred $X^1$—H compounds are selected from the group consisting of $R^2O$—H, $R^2(=O)O$—H, $R^2_2C=NO$—H, and $R^2_2NO$—H, wherein each $R^2$ is independently selected from the group consisting of hydrogen, straight, cyclic or branched alkyl, alkenyl, aryl and aralkyl groups wherein each $R^2$, other than hydrogen, contains from 1 to 18 carbon atoms and optionally at least one heteroatom selected from the group consisting of oxygen and sulfur.

The amount of $X^1$—H used in step (c) is typically at stoimetric amounts or in excess, based upon the amount of Si—$X^4$. Preferably, the amount of $X^1$—H is from about 1.0 mole to about 10 moles of $X^1$—H per mole of $SiX^4$, and more preferably, from about 1.5 moles to 5 moles of $X^1$—H per mole of $SiX^4$. The excess reagent, $X^1$—H, helps drive the reaction to completion.

The reaction can be carried out at sub-ambient, ambient or elevated temperatures, and at sub-atmospheric, atmospheric and supra-atmospheric pressures. When $X^1$—H is $R^2O$—H, the $X^4$—H catalyzes its decomposition and generates water, a undesirable side reaction. Therefore, it is preferred to carry out the reaction at elevated temperatures and sub-atmospheric pressure or atmospheric pressure in order to remove the $X^4$—H as it is formed. Preferably, the reaction is carried out room temperature (about 20° C.) to 150° C. and pressures ranging from about 0.5 torr to 1 atmosphere, and more preferably from about 50° C. to 100° C. and 2 torr to 500 torr. Generally, if a solvent is desired, excess $X^1$—H can be used.

Another embodiment of the invention is directed to a composition comprising: at least one filler; and at least one silane of Formula (1) in admixture with, or chemically bonded, to the filler.

Another embodiment of the invention is directed to a rubber composition containing an activated halo-containing aralkyl silane. The rubber composition comprises:

(a) at least one rubber component;
(b) at least one filler;
(c) optionally, at least one activating agent; and,
(d) at least one halo-containing aralkylsilane of the generalized structural Formula (1):

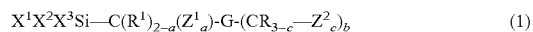  (1)

wherein:

$X^1$ is a hydrolyzable moiety selected from the group consisting of Cl—, Br—, I—, $R^2O$—, $R^2(=O)O$—, $R^2_2C=NO$—, and $R^2_2NO$—, wherein each $R^2$ is independently selected from the group consisting of hydrogen, straight, cyclic or branched alkyl, alkenyl, aryl and aralkyl groups wherein each $R^2$, other than hydrogen, contains from 1 to 18 carbon atoms and optionally at least one heteroatom selected from the group consisting of oxygen and sulfur;

each occurrence of $X^2$ and $X^3$ is independently selected from $X^1$ and $R^3$ groups wherein each $R^3$ is independently selected from the group consisting of hydrogen, alkyl, alkenyl, aryl and aralkyl groups wherein each $R^3$, other than hydrogen, contains from 1 to 18 carbon atoms and optionally at least one heteroatom selected from the group consisting of oxygen and sulfur;

$R^1$ is selected from the group consisting of hydrogen, alkyl, alkenyl, aryl and aralkyl wherein $R^1$, other than hydrogen, contains from 1 to 10 carbon atoms;

each occurrence of $Z^1$ and $Z^2$ is independently a halogen atom selected from the group consisting of F—, Cl—, Br— and I—;

G is a monovalent or polyvalent aromatic hydrocarbon group of Formula (2):

  (2)

wherein the six carbon atoms are part of an aromatic ring structure and each occurrence of $R^4$ is independently selected from the group consisting of hydrogen, alkyl, alkenyl, aryl and aralkyl groups wherein each $R^4$, other than hydrogen, contains from 1 to 18 carbon atoms;

each occurrence of R is independently selected from the group consisting of hydrogen, alkyl, alkenyl, aryl and aralkyl wherein each R, other than hydrogen, contains from 1 to 30 carbon atoms; and, a, b and c are integers whereby a is 1; b is from 0 to 5; and c is from 1 to 3.

There is also provided herein a process of preparing the above-described rubber composition comprising mixing components (a), (b), optionally (c), and (d).

The rubber composition of the present invention can optionally contain one or more other hydrolyzable organosilanes that hydrophobate and aid in the dispersion of silane-reactive filler (b). These hydrolyzable organosilanes contain at least one alkyl group, preferably of from 3 to 18 carbon atoms and more preferably from about 6 to 10 carbon atoms, and at least one $R^7O$— hydrolyzable group wherein $R^7$ is hydrogen or an alkyl, alkenyl, aryl or aralkyl of from 1 to 10 carbon atoms. These hydrolyzable organosilanes can be used, e.g., preferably in amounts of from about 0.5 to about 10 phr and more preferably in amounts of from about 1 to about 5 phr.

The rubber composition herein comprises the mixture and/or reaction product of components (a), (b), optionally (c), and (d).

In a further embodiment herein, in the rubber composition silane (d) bonds to filler (b) through one functionality and to rubber component (a) (e.g., diene polymer) through a different functionality.

In one embodiment, at least one activating agent (c) can be used in the rubber compounding process to facilitate the coupling reactions between rubber component (a) and silane (d). The activating agent can be selected from among the transition metal salts. Transition metal salts are compounds that assist in the removal of the $Z^1$ and $Z^2$ group on the silane of general Formula (1) and include metal oxides, metal halides, metal carboxylates, metal hydroxides and other suitable metal complexes. Some representative non-limiting examples of transition metal salts include metal oxides such as zinc oxide, aluminum oxide, and titanium oxide; metal halides, such as zinc chloride, zinc bromide, zinc iodide, aluminum chloride, aluminum bromide, titanium chloride, titanium bromide and stannic chloride; and, metal carboxylates such as zinc stearate, zinc acetate and stannic octanoate.

In one embodiment herein, rubber component (a) can be an organic polymer selected from the group consisting of at least one diene based elastomer and rubber. In one embodiment herein, rubber component (a) can be any of those that are well known in the art many of which are described in "The Vanderbilt Rubber Handbook", R. F. Ohm, ed.; R. T. Vanderbilt Company, Inc., Norwalk, Conn., 1990 and "Manual For The Rubber Industry", T. Kempermann, S. Koch, J. Sumner, eds.; Bayer AG, Leverkusen, Germany, 1993, the entire content of both enclosed by reference. In yet another further embodiment, some representative non-limiting examples of suitable rubber component (a) (organic polymers) include natural rubber (NR), synthetic polyisoprene (IR), polybutadiene (BR), various copolymers of butadiene, the various copolymers of isoprene and mixtures of these elastomers; solution styrene-butadiene rubber (SSBR), emulsion styrene-butadiene rubber (ESBR), ethylene-propylene terpolymers (EPDM) and acrylonitrile-butadiene rubber (NBR).

In one embodiment herein, rubber component (a) is comprised of at least one diene-based elastomer or rubber. In an even more specific embodiment, suitable monomers for preparing the rubbers are conjugated dienes such as the non-limiting examples of isoprene and 1,3-butadiene, and suitable vinyl aromatic compounds such as the non-limiting examples of styrene and alpha methyl styrene, and combinations thereof. In a particular embodiment, rubber component (a) is a sulfur-curable rubber. In a further embodiment, the diene based elastomer, or rubber, can be selected from the non-limiting examples of at least one of cis-1,4-polyisoprene rubber (natural and/or synthetic), and preferably natural rubber, emulsion polymerization-prepared styrene/butadiene copolymer rubber, organic solution polymerization-prepared styrene/butadiene rubber, 3,4-polyisoprene rubber, isoprene/butadiene rubber, styrene/isoprene/butadiene terpolymer rubber, cis-1,4-polybutadiene, medium vinyl polybutadiene rubber (about 35-50 percent vinyl), high vinyl polybutadiene rubber (about 50-75 percent vinyl), styrene/isoprene copolymers, emulsion polymerization-prepared styrene/butadiene/acrylonitrile terpolymer rubber and butadiene/acrylonitrile copolymer rubber. An emulsion polymerization-derived styrene/butadiene (ESBR) is also contemplated as diene-based rubber for use herein such as one having a relatively low to medium styrene content of from about 20 to about 29 percent bound styrene or, for some applications, an ESBR having a medium to relatively high bound styrene content, in particular, a bound styrene content of from about 30 to about 45 percent. In an even further specific embodiment, emulsion polymerization-prepared styrene/butadiene/acrylonitrile terpolymer rubbers containing from about 2 to about 40 weight percent bound acrylonitrile in the terpolymer are also contemplated as diene-based rubbers for use herein.

In another embodiment herein, the solution polymerization-prepared SBR (SSBR) typically has a bound styrene content in a range of preferably from about 5 to about 50, more preferably from about 9 to about 36 bound styrene and most preferably from about 20 to about 30 weight percent bound styrene. In a more specific embodiment, polybutadiene elastomer can be conveniently characterized, for example, by having at least about 90 weight percent cis-1,4-content.

In still another embodiment herein, rubber component (a) is a diene polymer functionalized or modified by an alkoxysilane derivative. Silane-functionalized organic solution polymerization-prepared styrene-butadiene rubber and silane-functionalized organic solution polymerization-prepared 1,4-polybutadiene rubbers may be used. These rubber compositions are known; see, for example U.S. Pat. No. 5,821,290 the entire contents of which are incorporated by reference herein.

In yet another embodiment herein, rubber component (a) is a diene polymer functionalized or modified by a tin derivative. Tin-coupled copolymers of styrene and butadiene may be prepared, for example, by introducing a tin coupling agent during the styrene and 1,3-butadiene monomer copolymerization reaction in an organic solvent solution, usually at or near the end of the polymerization reaction. Such tin coupled styrene-butadiene rubbers are well known to those skilled in the art; see, for example U.S. Pat. No. 5,268,439, the entire contents of which are incorporated by reference herein. In practice, at least about 50 percent, and more preferably from about 60 to about 85 percent, of the tin is bonded to the butadiene units of the styrene-butadiene rubbers to create a tin-dienyl bond.

In still yet another embodiment, rubber component (a) is selected from the group comprising natural rubber and synthetic polyisoprene.

In an embodiment, the filler (b) of the rubber composition and/or the filler/silane composition of the invention (referred to for simplicity as "filler (b)") is a silane-reactive filler. The expression "silane-reactive filler" shall be understood to mean a substance that is capable of reacting with silane (d) to form stable Si—O-filler bonds. The silane-reactive filler includes a substance that is added to rubber component (a) to reinforce the elastomeric network. Reinforcing fillers are materials whose moduli are higher than rubber component (a) of the rubber composition and are capable of absorbing stress from rubber component (a) when this component is strained. In one embodiment, silane-reactive filler (b) includes fibers, particulates and sheet-like structures and can be composed of inorganic minerals, silicates, silica, clays, ceramics, carbon, organic polymers and diatomaceous earth. In one embodiment, silane-reactive filler (b) can be a discrete particle or group of particles in the form of aggregates or agglomerates. Silane-reactive filler (b) can be mixed with other fillers that do not react with silane (d). These fillers are used to either extend rubber component (a) or to reinforce the elastomeric network. Some representative non-limiting examples of suitable silane-reactive filler (b) materials include at least one metal oxide such as silica (pyrogenic and/or precipitated), titanium dioxide, aluminosilicate, alumina and siliceous materials including clays and talc. In a specific embodiment herein, particulate precipitated silica is sometimes used in connection with a silane. In one embodiment, silane-reactive filler (b) is a silica used alone or in combination with one or more other fillers. In another specific embodiment, in one non-limiting embodiment, a combination of silica and carbon black is utilized, such as for reinforcing fillers for various rubber products, including the non-limiting example of treads for tires. In another embodiment, alumina can be used either alone or in combination with silica. The term "alumina" herein refers to aluminum oxide, or $Al_2O_3$. In a further specific embodiment, the fillers can be hydrated or in anhydrous form. Use of alumina in rubber compositions is known; see, for example, U.S. Pat. No. 5,116,886 and EP 631 982, the entire contents of both of which are incorporated by reference herein.

In one embodiment, the term "carrier" as used herein means a porous or high surface area filler or organic polymer that has a high adsorption or absorption capability and is capable of carrying up to about 75 percent liquid silane while maintaining its free-flowing and dry properties. In one embodiment, the carrier filler or carrier polymer herein is essentially inert to the silane and is capable of releasing or deabsorbing the liquid silane when added to the elastomeric composition.

In one embodiment, silane-reactive filler (b) herein can be used as a carrier for liquid silanes and reinforcing fillers for elastomers in which silane (d) herein is capable of reacting or bonding with the surface. In another embodiment, the fillers that are used as carriers are non-reactive with the silanes of this invention. In a particular embodiment, the non-reactive nature of the fillers is demonstrated by the ability of silane (d) to be extracted at greater than about 50 percent of the loaded silane using an organic solvent. In a specific embodiment, the extraction procedure is described in U.S. Pat. No. 6,005,027, the entire contents of which are incorporated herein by reference. In one embodiment, carriers include, but are not limited to, porous organic polymers, carbon black, diatomaceous earth and silicas that are characterized by a relatively low differential of less than 1.3 between the infrared absorbance at 3502 $cm^{-2}$ of the silica when taken at 105° C. and when taken at 500° C. as described in U.S. Pat. No. 6,005,027, the entire contents of which are incorporated herein by reference.

In one embodiment, the amount of silane (d) that can be loaded on the carrier is between about 0.1 and about 70 percent. In another embodiment, silane (d) is loaded on the carrier at concentrations between about 10 and about 50 percent.

In one non-limiting embodiment herein, silane-reactive filler (b) includes fillers in which the silane (d) is reactive with the surface of the filler. In a specific embodiment herein, particulate precipitated silica is useful as silane-reactive filler (b), particularly when the silica has reactive surface silanols. In a further embodiment herein, the silane-reactive filler (b) herein may be in the hydrated form.

In one non-limiting embodiment herein, the other fillers that may be mixed with silane-reactive filler (b) can be essentially inert to the silane (d) with which they are admixed as is the case with carbon black or organic polymers, or at least two silane-reactive fillers can be mixed together and can be reactive therewith, e.g., the case with carriers possessing metal hydroxyl surface functionality, e.g., silicas and other siliceous particulates which possess surface silanol functionality, in combination with reinforcing fillers containing metal hydroxyl surface functionality, e.g., alumina, silicas and other siliceous fillers.

In one embodiment herein, precipitated silica is utilized as silane-reactive filler (b). In a more specific embodiment, the silica filler herein can be characterized by having a Brunauer, Emmett and Teller (BET) surface area, as measured using nitrogen gas, preferably in the range of from about 40 to about 600 $m^2/g$, and more preferably in a range of from about 50 to about 300 $m^2/g$ and most preferably in a range of from about 100 to about 150 $m^2/g$. The BET method of measuring surface area described in the Journal of the American Chemical Society, Volume 60, page 304 (1930) and is the method used herein. In yet another specific embodiment, the silica typically can also be characterized by having a dibutylphthalate (DBP) absorption value in a range of preferably from about 100 to about 350, more preferably from about 150 to about 300 and most preferably from about 200 to about 250. In an even further specific embodiment, silane-reactive fillers (b), as well as the aforesaid alumina and aluminosilicate fillers, can be expected to have a CTAB surface area in a range of from about 100 to about 220 $m^2/g$. The CTAB surface area is the external surface area as determined by cetyl trimethylammonium bromide with a pH of 9; the method for its measurement is described in ASTM D 3849.

Mercury porosity surface area is the specific surface area determined by mercury porosimetry. In this technique, mercury is penetrated into the pores of the sample after a thermal treatment to remove volatiles. In a more specific embodiment, set-up conditions use a 100 mg sample, remove volatiles over 2 hours at 105° C. and ambient atmospheric pressure and employ a measuring range of from ambient to 2000 bars pressure. In another embodiment, such evaluation can be performed according to the method described in Winslow, et al. in ASTM bulletin, p. 39 (1959) or according to DIN 66133; for such an evaluation, a CARLO-ERBA Porosimeter 2000 can be used. In one embodiment, the average mercury porosity specific surface area for the selected silane-reactive filler (b) (e.g., silica) should be in a range of, preferably, from about 100 to about 300 $m^2/g$, more preferably from about 150 to about 275 $m^2/g$ and most preferably from about 200 to about 250 $m^2/g$.

In one embodiment, a suitable pore size distribution for the silane-reactive filler (b) (e.g. the non-limiting examples of silica, alumina and aluminosilicate) according to such mercury porosity evaluation is considered herein to be: five percent or less of its pores having a diameter of less than about 10 nm; from about 60 to about 90 percent of its pores have a diameter of from about 10 to about 100 nm; from 10 to about 30 percent of its pores having a diameter of from about 100 to about 1,000 nm; and from about 5 to about 20 percent of its pores have a diameter of greater than about 1,000 nm. In a second embodiment, the silane-reactive filler (b) (e.g., silica) can be expected to have an average ultimate particle size, for example, in the range of from about 0.01 to about 0.05 µm as determined by electron microscopy, although the particles (e.g., silica) can be even smaller, or possibly larger, in size. In one embodiment, various commercially available silicas can be considered for use herein such as those available from PPG Industries under the HI-SIL trademark, in particular, HI-SIL 210, and 243; silicas available from Rhone-Poulenc, e.g., ZEOSIL 1165MP; silicas available from Degussa, e.g., VN2 and VN3, etc. and silicas available from Huber, e.g., HUBER-SIL 8745.

In one embodiment, where it is desired for a rubber composition which contains both a siliceous filler such as silica, alumina and/or aluminosilicates and also carbon black reinforcing pigments, to be primarily reinforced with silica as the reinforcing pigment, it is often more specific that the weight ratio of such siliceous fillers to carbon black is at least about 3/1 and preferably at least about 10/1 and, thus, in a range of from about 3/1 to about 30/1. In a more specific embodiment, silane-reactive filler (b) can comprise from about 15 to about 95 weight percent precipitated silica, alumina and/or aluminosilicate and, correspondingly, from about 5 to about 85 weight percent carbon black having a CTAB value in a range of from about 80 to about 150. In one specific embodiment, alternatively, silane-reactive filler (b) can comprise from about 60 to about 95 weight percent of said silica, alumina and/or aluminosilicate and, correspondingly, from about 40 to about 5 weight percent of carbon black. In another specific embodiment, the siliceous filler and carbon black can be pre-blended or blended together in the manufacture of the vulcanized rubber.

In one embodiment, there is provided herein a process for preparing a rubber composition comprising mixing components (a), (b), optionally (c), and (d), as defined herein, in effective amounts. In one embodiment herein, an effective amount of silane (d) is preferably from about 0.2 to about 20, more preferably from about 0.5 to about 15 and most preferably from about 2 to about 10 weight percent of silane (d) based on the total weight of rubber composition herein. In another embodiment, an effective amount of silane-reactive filler (b) is preferably from about 2 to about 70, more preferably from about 5 to about 50 and most preferably from about 20 to about 40 weight percent of silane-reactive filler (b) wherein said weight percent is based on the total weight of rubber composition herein. In yet another embodiment herein, an effective amount of rubber component (a) is preferably from about 30 to about 98, more preferably from about 50 to about 95 and most preferably from about 60 to about 80 weight percent of rubber component (a) based on the total weight of the rubber composition herein. In another embodiment herein, the herein described process for preparing a rubber composition can further comprise curing the rubber composition, before, during and/or after molding the rubber composition. In one embodiment herein, a vulcanized rubber composition should contain a sufficient amount of silane-reactive filler (b) to contribute a reasonably high modulus and high resistance to tear thereto. In a specific embodiment, the combined weight of silane-reactive filler (b) can be as low as about 5 to about 100 parts per hundred of rubber (phr) component (a), but is more preferably from about 25 to about 85 phr, and most preferably from about 50 to about 70 phr.

In one embodiment, silane (d) can be premixed, or pre-reacted, with particles, aggregates and/or agglomerates of silane-reactive filler (b) or added to the rubber mix during the processing or mixing of rubber (a) and silane-reactive filler (b). In another embodiment, if silane (d) and silane-reactive filler (b) are added separately to the process mixture during the rubber component (a) and silane-reactive filler (b), silane (d) can be considered to couple in situ to silane-reactive filler (b).

In one embodiment herein, in practice, sulfur vulcanized rubber products typically are prepared by thermomechanically mixing rubber and various ingredients in a sequentially step-wise manner followed by shaping and curing the compounded rubber to form a vulcanized product. In a more specific embodiment, first, for the aforesaid mixing of the rubber component (a) and various ingredients, typically exclusive of sulfur and sulfur vulcanization accelerators (collectively "curing agents"), the rubber(s) and various rubber compounding ingredients are usually blended in at least one, and optionally two or more, preparatory thermomechanical mixing stage(s) in suitable mixers. Such preparatory mixing is referred to as non-productive mixing or non-productive mixing steps or stages. In a more specific embodiment, such preparatory mixing usually is conducted at temperatures preferably in the range of from about 130° C. to about 180° C. and more preferably in the range of from about 140° C. to about 160° C.

In one embodiment, subsequent to such preparatory mixing stages, in a final mixing stage, sometimes referred to as a productive mixing stage, curing agents, and, optionally, one or more additional ingredients, are mixed with the rubber compound or composition, typically at a temperature in the range of from about 50° C. to about 130° C. which is a lower temperature than those utilized in the preparatory mixing stages, to prevent or retard premature curing of the sulfur-curable rubber, sometimes referred to as scorching of the rubber composition.

In another embodiment, the rubber composition typically is allowed to cool, sometimes after or during a process of intermediate mill mixing, between the aforesaid various mixing steps, for example, to a temperature of about 50° C. or lower.

In another embodiment herein, when it is desired to mold and to cure the rubber composition, the rubber composition is placed in the desired mold and heated to at least about 130° C. and up to about 200° C. causing the vulcanization of the rubber.

By thermomechanical mixing is meant that the rubber compound, or composition of rubber and rubber compounding ingredients, is mixed in a rubber mixer under high shear conditions where it autogenously heats up as a result of the mixing, primarily due to shear and associated friction within the rubber mixture in the rubber mixer. In one embodiment, several chemical reactions can occur at various steps in the mixing and curing processes.

In one embodiment, for example, the independent addition of a sulfur source can be manipulated by the amount of addition thereof and by sequence of addition relative to addition of other ingredients to the rubber mixture.

In another embodiment herein, the rubber composition herein can be prepared by a process comprising the steps of:
  a) thermomechanically mixing, in at least one preparatory mixing operation, in a first embodiment to a temperature of from about 140° C. to about 180° C. and in a second embodiment to a temperature of from about 150° to about 170° for a total mixing time in a first embodiment of from about 1 to about 20 minutes and in a second embodiment from about 4 to about 15 minutes, for such mixing operation(s):

i) about 100 parts by weight of at least one sulfur vulcanizable rubber selected from the group consisting of conjugated diene homopolymers and copolymers and copolymers of at least one conjugated diene and aromatic vinyl compound, ii) from about 5 to about 100 parts by weight of silane-reactive filler (b) in a first embodiment and from about 25 to 80 parts by weight of silane-reactive filler (b) in a second embodiment, wherein the silane-reactive filler (b) preferably contains from 0 to about 85 weight percent carbon black, and, iii) from about 0.05 to about 20 parts by weight rubber of at least one silane (d) of general Formula (1) as described above in a first embodiment and from about 2 to 10 parts by weight rubber in a second embodiment;

iv) optionally, from about 0.01 to about 15 parts by weight activator (c) in a first embodiment and from about 1 to about 5 parts by weight activator (c) in a second embodiment;

b) blending the mixture from step (a), in a final thermomechanical mixing step, at a temperature of from about 50° C. to about 130° C. for a time sufficient to blend the rubber component (a), e.g., for from about 1 to about 30 minutes in a first embodiment and for about 1 to about 5 minutes in a second embodiment, and a curing agent at 0 to about 5 parts by weight; and, c) optionally curing said mixture at a temperature in the range of from about 130° C. to about 200° C. for a period of from about 5 to about 60 minutes.

The rubber composition herein can be compounded by methods known in the rubber compounding art such as mixing component (a) (the various sulfur-vulcanizable constituent rubbers) with various commonly used additive materials such as, for example, curing aids such as sulfur, activators, retarders and accelerators, processing additives such as oils, resins, e.g., tackifying resins, silicas, plasticizers, fillers, pigments, fatty acid, zinc oxide, waxes, antioxidants and antiozonants, peptizing agents, and reinforcing materials such as, for example, carbon black, and the like. Depending on the intended use of the rubber composition (sulfur-vulcanizable) and cured rubber composition (sulfur-vulcanized material), the aforementioned additives are selected and commonly used in conventional amounts.

Vulcanization can be conducted in the presence of an additional sulfur vulcanizing agent. In one specific embodiment, some non-limiting examples of suitable sulfur vulcanizing agents include, e.g., elemental sulfur (free sulfur) or sulfur-donating vulcanizing agents such as the non-limiting examples of amino disulfide, polymeric polysulfide or sulfur-olefin adducts, which are conventionally added in the final, i.e., productive, rubber composition mixing step. In another specific embodiment, the sulfur vulcanizing agents (which are common in the art) are used, or added, in the productive mixing stage, in an amount ranging from about 0.4 to about 3 phr, or even in some circumstances, up to about 8 phr, with a range of from about 1.5 to about 2.5 phr, and in some cases from about 2 to about 2.5 phr, being generally suitable.

Vulcanization accelerators, i.e., additional sulfur donors, can also be used if desired. Non-limiting examples of vulcanization accelerators include benzothiazole, alkyl thiuram disulfide, guanidine derivatives and thiocarbamates. Other examples, representative of such accelerators include, but are not limited to, mercapto benzothiazole, tetramethyl thiuram disulfide, benzothiazole disulfide, diphenylguanidine, zinc dithiocarbamate, alkylphenoldisulfide, zinc butyl xanthate, N-dicyclohexyl-2-benzothiazolesulfenamide, N-cyclohexyl-2-benzothiazolesulfenamide, N-oxydiethylenebenzothiazole-2-sulfenamide, N,N-diphenylthiourea, dithiocarbamyl-sulfenamide, N,N-diisopropylbenzothiozole-2-sulfenamide, zinc-2-mercaptotoluimidazole, dithiobis(N-methylpiperazine), dithiobis(N-beta-hydroxy ethyl piperazine), dithiobis (dibenzyl amine) and combinations thereof. In another embodiment, other additional sulfur donors, include, e.g., thiuram and morpholine derivatives. In a more specific embodiment, representative of such donors include, e.g., but are not limited to, dimorpholine disulfide, dimorpholine tetrasulfide, tetramethyl thiuram tetrasulfide, benzothiazyl-2,N-dithiomorpholide, thioplasts, dipentamethylenethiuram hexasulfide, disulfidecaprolactam and combinations thereof.

Accelerators are used to control the time and/or temperature required for vulcanization and to improve the properties of the vulcanizate. In one embodiment, a single accelerator system can be used, i.e., a primary accelerator. In another embodiment, conventionally and more specifically, a primary accelerator(s) is used in total amounts ranging from about 0.5 to about 4, preferably from about 0.8 to about 1.5 phr. In a more specific embodiment, combinations of a primary and a secondary accelerator can be used with the secondary accelerator being used in smaller amounts (e.g., from about 0.05 to about 3 phr) in order to activate and to improve the properties of the vulcanizate. In yet a another embodiment, delayed action accelerators can also be used. In yet another embodiment, vulcanization retarders can also be used. In one embodiment, suitable types of accelerators are those such as the non-limiting examples of amines, disulfides, guanidines, thioureas, thiazoles, thiurams, sulfenamides, dithiocarbamates, xanthates and combinations thereof. In a more specific embodiment, the primary accelerator is a sulfenamide. In another specific embodiment, if a second accelerator is used, the secondary accelerator is a guanidine, dithiocarbamate or thiuram compound.

Optional tackifier resins can be used at levels of from about 0.5 to about 10 phr, and usually from about 1 to about 5 phr. In one specific embodiment, typical amounts of processing aids comprise from about 1 to about 50 phr. Suitable processing aids can include, as non-limiting examples, aromatic, naphthenic and/or paraffinic processing oils and combinations thereof. In yet another specific embodiment, typical amounts of antioxidants are from about 1 to about 5 phr. Representative antioxidants include, as non-limiting examples, diphenyl-p-phenylenediamine and others, e.g., those disclosed in the Vanderbilt Rubber Handbook (1978), pages 344-346. In yet another embodiment, typical amounts of antiozonants are from about 1 to about 5 phr. Typical amounts of optional fatty acids, which can include the non-limiting example of stearic acid, are from about 0.5 to about 3 phr. In one embodiment, typical amounts of zinc oxide are from about 2 to about 5 phr. In yet another specific embodiment, typical amounts of waxes, e.g., microcrystalline wax, are from about 1 to about 5 phr. Typical amounts of peptizers are from about 0.1 to about 1 phr. Suitable peptizers include, as non-limiting examples, pentachlorothiophenol, dibenzamidodiphenyl disulfide and combinations thereof.

The rubber compositions herein can be used for various purposes. In one specific embodiment herein, there is provided an article of which at least one component is the herein described cured rubber composition. In another specific embodiment herein, there is provided a tire at least one component of which, e.g., the tread, comprises the herein described cured rubber composition. In yet another specific embodiment, for example, the rubber composition herein can be used for the manufacture of such articles as shoe soles, hoses, seals, cable jackets, gaskets and other industrial goods. Such articles can be built, shaped, molded and cured by various known and conventional methods as is readily apparent to those skilled in the art.

The invention can be better understood by reference to the following examples in which the parts and percentages are by weight unless otherwise indicated.

EXAMPLES

Synthesis of the Coupling Agents

Example 1

Preparation of (1-p-tolyl-ethyl)trichlorosilane

Into a 3 liter round-bottom flask fitted with a reflux condenser, addition funnel and magnetic stir bar, was charged 4-methylstyrene (900 g, 7.6 mols) and Bis(triphenylphosphine)palladium (II) dichloride (1.8 g, 0.2% wt). The reaction mixture was heated to 70° C. and then trichlorosilane (1031 g, 7.6 mols) was added dropwise to the reaction mixture. During the addition, the reaction mixture was maintained between 80 to 100° C. After the addition was finished, the reaction mixture was kept at 70° C. for additional two hours. After distillation, pure (1-p-tolyl-ethyl)trichlorosilane (1400 g, 5.53 mols) was obtained (collected at 75° C./1 mmHg). The product structure was characterized by GC-MS and $^{13}$C NMR ($\delta$~14 ppm, CDCl$_3$, Cl$_3$Si—CH(CH$_3$)-Ph; $\delta$~35 ppm, CDCl$_3$, Cl$_3$Si—CH(CH$_3$)-Ph).

Comparative Example 2

Preparation of (2-p-tolyl-ethyl)trichlorosilane

Into a 3 liter round-bottom flask fitted with a reflux condenser, addition funnel and magnetic stir bar, was charged 4-methylstyrene (904.4 g, 7.65 mols), VCAT (2.25 g, 50 ppm) and phenothiazine (1.94 g, 1000 ppm). The reaction mixture was heated to 70° C. and then trichlorosilane (1036.6 g, 7.65 mols) was added dropwise to the reaction mixture. During the addition, the reaction mixture was maintained between 80 to 100° C. After the addition was finished, the reaction mixture was kept at 70° C. for additional two hours. After distillation, >98% pure (2-p-tolyl-ethyl)trichlorosilane (1565 g, 6.19 mols) was obtained (collected at 75° C./1 mmHg). The product structure was characterized by GC-MS.

Example 3

Preparation of (1-phenylethyl)trichlorosilane

Into a 2-liter round-bottom flask fitted with a reflux condenser, addition funnel and magnetic stir bar, was charged styrene (410 g, 3.94 mols) and Bis(triphenylphosphine)palladium (II) dichloride (1.2 g, 0.3% wt). The reaction mixture was heated to 70° C. and then trichlorosilane (532.8 g, 3.94 mols) was added dropwise to the reaction mixture. During the addition, the reaction mixture was maintained between 80 to 110° C. After the addition was finished, the reaction mixture was kept at 70° C. for additional two hours. After distillation, >98% pure (1-phenylethyl)trichlorosilane (840 g, 99% purity) was obtained (collected at 78° C./3 mmHg). The product structure was characterized by GC-MS.

Example 4

Chlorination of (1-p-tolyl-ethyl)trichlorosilane using lauroyl peroxide and Cl$_2$ (1-p-Tolyl-ethyl)trichlorosilane (100 g, 0.4 mol) and lauroyl peroxide (1.0 g, 1% wt of silane) were charged into a reaction flask. Under stirring, Chlorine gas from a lecture bottle was then introduced by bubbling into the reaction mixture at room temperature. The reaction temperature was controlled under 40° C. until the chlorine gas bubbling was stopped after one hour of Cl$_2$ input. GC spectra indicate that a mixture of chlorinated products trichloro-[1-(4-chloromethyl-phenyl)-ethyl]-silane, trichloro-(1-chloro-1-p-tolyl-ethyl)-silane and trichloro-[1-chloro-1-(4-chloromethyl-phenyl)-ethyl]-silane with the ratio of 2.6:1.7:1.0 was obtained. The product structures were characterized by GC-MS and $^{13}$C NMR (for example, $\delta$~45 ppm, CDCl$_3$, Ph-CH$_2$Cl). Longer reaction with Cl$_2$ gas leads to formation of products with high levels of chlorination.

Example 5

Chlorination of (1-p-tolyl-ethyl)trichlorosilane using PCl$_5$ and Cl$_2$ (1-p-Tolyl-ethyl)trichlorosilane (100 g, 0.4 mol) and PCl$_5$ (1.0 g, 1% wt of silane) were charged into a reaction flask. Under stirring, Chlorine gas from a lecture bottle was then introduced by bubbling into the reaction mixture at room temperature. The reaction temperature was controlled under 40° C. until the Chlorine gas bubbling was stopped. After one hour of Cl$_2$ input, GC spectra indicate a mixture of products, trichloro-[1-(4-chloromethyl-phenyl)-ethyl]-silane, trichloro-(1-chloro-1-p-tolyl-ethyl)-silane and trichloro-[1-chloro-1-(4-chloromethyl-phenyl)-ethyl]-silane, was obtained with the ratio of 3.6:2.0:1.0. The product structures were characterized by GC-MS.

Example 6

Chlorination of (1-p-tolyl-ethyl)trichlorosilane using PCl$_5$, lauroyl peroxide and Cl$_2$ (1-p-Tolyl-ethyl)trichlorosilane (100 g, 0.4 mol), lauroyl peroxide (1.0 g, 1% wt of silane) and PCl$_5$ (1.0 g, 1% wt of silane) were charged into a reaction flask. Under stirring, chlorine gas from a lecture bottle was then introduced by bubbling into the reaction mixture at room temperature. The reaction temperature was controlled under 40° C. until the chlorine gas bubbling was stopped. After one hour of Cl$_2$ input, GC spectra indicate a mixture of products, trichloro-[1-(4-chloromethyl-phenyl)-ethyl]-silane, trichloro-(1-chloro-1-p-tolyl-ethyl)-silane and trichloro-[1-chloro-1-(4-chloromethyl-phenyl)-ethyl]-silane, was obtained with the ratio of 3.2:1.7:1.0. The product structures were characterized by GC-MS.

Example 7

Bromination of (1-p-tolyl-ethyl)trichlorosilane using bromine (1-p-Tolyl-ethyl)trichlorosilane (25.3 g, 0.1 mol) in 100 ml heptane was charged into a 500 ml 3-neck reaction flask equipped with a thermal control, addition funnel and reflux. The pot was heated to 70° C. under stirring, then bromine (16 g, 0.1 mol) in 100 ml heptane was added drop wise into the reaction mixture. The brown color of bromine disappeared immediately after the addition. When the bromine addition was finished, the reaction mixture was kept at 70° C. for 2 more hours. GC spectra of the reaction mixture indicated that the product contained unreacted starting materials and brominated products, trichloro-[1-(methyl-phenyl)-ethyl]-silane, trichloro-[1-(4-bromomethyl-phenyl)-ethyl]-silane, trichloro-(1-bromo-1-p-tolyl-ethyl)-silane and trichloro-[1-bromo-1-(4-chloromethyl-phenyl)-ethyl]-silane, with the ratio of 1.0:0.83:0.44:0.20. The product structures were characterized by GC-MS.

Example 8

Transesterification of the Reaction Product of Example 6

Chlorinated trichlorosilanes prepared from Example 6 (589 grams) was charged into a 3 L round-bottomed flask equipped with a magnetic stirrer, distillation head and receiver flask. The reaction vessel was heated at 50° C. under a vacuum of initially 200 mmHg while ethanol (707 g) was added dropwise to the vessel. When the addition was finished, excess ethanol was distilled out and the corresponding triethoxysilane mixture (642 g) was obtained as clear liquid. The product structures were characterized by GC-MS.

Example 9

Transesterification of the Distilled Reaction Product of Example 6

Distilled reaction product of Example 6 containing no unreacted (1-p-tolyl-ethyl)trichlorosilane (316 grams) was charged into a 2 L round-bottomed flask equipped with a magnetic stirrer, distillation head and receiver flask. The reaction vessel was heated at 50° C. under a vacuum of initially 200 mmHg while ethanol (379 g) was added drop wise to the vessel. When the addition was finished, excess ethanol was distilled out and the corresponding triethoxysilane mixture (348 g) was obtained as clear liquid. The product structures were characterized by GC-MS.

Examples Comparative 10 and 11, Examples 12 and 13

Preparation of the Rubber Compositions

In the following examples, the amounts of reactants were parts per hundred of rubber (phr) unless otherwise indicated. The following rubber compositions were prepared based on natural rubber and reinforced with highly dispersible precipitated silica, the said compositions being intended for tread compounds in truck tires. Formulations for the rubber compositions of these examples are described below in Table 1. The rubber compositions contained silica as the reinforcing filler.

TABLE 1

Formulations of the Rubber Compositions

| Composition No. | Comparative Example 10 | Comparative Example 11 | Example 12 | Example 13 |
|---|---|---|---|---|
| NR | 100 | 100 | 100 | 100 |
| Silica | 58 | 58 | 58 | 58 |
| CB | 3 | 3 | 3 | 3 |
| Silquest* A-1289 silane | 4.5 | | | |
| ((m,p-chloromethyl-phenyl)ethyl)triethoxysilane | | 5.0 | | |
| Silane from Example 8 | | | 5.0 | |
| Silane from Example 9 | | | | 5.0 |
| Process oil | 5.0 | 5.0 | 5.0 | 5.0 |
| ZnO | 4.0 | 4.0 | 4.0 | 4.0 |
| Stearic Acid | 2.0 | 2.0 | 2.0 | 2.0 |
| 6 PPD | 2.5 | 2.5 | 2.5 | 2.5 |
| Naugurd Q | 2.0 | 2.0 | 2.0 | 2.0 |
| Wax | 1.0 | 1.0 | 1.0 | 1.0 |
| Sulfur | 1.4 | 1.4 | 1.4 | 1.4 |
| TBBS | 1.6 | 1.6 | 1.6 | 1.6 |
| DPG | 2.0 | 2.0 | 2.0 | 2.0 |

The notation of Table 1 is defined as follows: NR: Natural rubber (SMR-L); silica: Zeosil 1165MP from Rhodia; CB: carbon black (N-220); process oil: Sundex 8125 from Sun Oil; ZnO: Kadox 720C from ZincCorp.; stearic acid: Industrene R from Witco, Crompton; 6 PPD: (Flexzone 7P from Uniroyal); Wax: Sunproof Improved from Uniroyal, Crompton; Naugurd Q: from Uniroyal; Sulfur: Rubbermakers Sulfur 104 from Harwick; TBBS: Delac S from Uniroyal, Crompton; DPG: from Uniroyal, Crompton; Silquest* A-1289 silane: from Momentive Performance Materials.

The mixing of the rubber masterbatch was done in a two-pass procedure as hereinafter described using a Krupp mixer with a 1550 cubic centimeter (cc) chamber volume. In the first pass, the mixer is turned on with the mixer at 30 rpm and the cooling water on full. The rubber polymers ware added to the mixer and ram down mixed for 60 seconds. Half of the silica and all of the silane with approximately 35-40 grams of this portion of silica in an ethylvinyl acetate (EVA) bag were added and ram down mixed for 60 seconds. The remaining silica and the processing oil in an EVA bag wee next added and ram down mixed for 60 seconds. The mixer throat was dusted down, and the mixer's mixing speed was increased to 90 rpm as required to raise the temperature of the rubber masterbatch to 140° C. The master batch was dumped (removed from the mixer), a sheet was formed on a roll mill set at about 60° to 65° C. and the sheet was allowed to cool to ambient temperature.

In the second pass, the sheets from the first pass were added to the mixer and ram down mixed for 60 seconds. The rest of the ingredients except for the curatives were added together and ram down mixed for 60 seconds. The mixer throat was dusted down and the mixer's mixing speed was increased to 90 rpm as is required to raise the temperature of the rubber master batch to between 135° C. to 140° C. The rubber master batch was mixed for five minutes and the speed of the Krupp mixer was adjusted to maintain the temperature between 135° C. and 140° C.

The rubber masterbatch and the curatives were mixed on a roll mill heated to between 60° C. and 65° C. The sulfur and accelerators were added to the rubber masterbatch, were thoroughly mixed on the roll mill and were allowed to form a sheet. The sheet is cooled to ambient before curing.

Measurements and Testing of the Rubber Compositions

The measurements to characterize the rubber compositions were described below. The rubber compositions are characterized before and after curing, as was indicated below.

The rheological properties of the compositions were measured on a Monsanto R-100 Oscillating Disk Rheometer and a Monsanto M1400 Mooney Viscometer. The specimens for measuring the mechanical properties were cut from 6 mm plaques cured for (t90+1) minutes at 149° C. Curing and testing of the cured rubber compositions in the form of plaques were carried out according to ASTM standards. In addition, small strain dynamic tests were carried out on a Rheometrics Dynamic Analyzer (ARES—Rheometrics Inc.). Payne effect strain sweeps were carried out from dynamic strain amplitudes of 0.01% to about 25% shear strain amplitude at 10 Hz and 60° C. The dynamic parameters, $G'_{initial}$, $\Delta G'$, $G''_{max}$ and $\tan \delta_{max}$, were extracted from the non-linear responses of the rubber compounds at small strains. In some cases, steady state values of tan δ were measured after 15 minutes of dynamic oscillations at strain amplitudes of 35% (at 60° C.). Temperature dependence of dynamic properties was also measured from about −80° C. to +80° C. at small strain amplitudes (1 or 2%) at a frequency of 10 Hz.

The specific curing procedure and measuring procedures were as follows:

| Curing Procedure/Measurement | Testing Standard |
|---|---|
| Mooney viscosity and scorch | ASTM D1646 |
| Oscillating disc rheometry | ASTM D2084 |
| Curing of test plaques | ASTM D3182 |
| Stress-strain properties | ASTM D412 |
| Heat build-up | ASTM D623 |

The results are presented in Table 2 to 4.

TABLE 2

Rheological properties of rubber compositions

| Composition No. | Comparative Example 10 | Comparative Example 11 | Example 12 | Example 13 |
|---|---|---|---|---|
| Viscosity at 100° C. (ML1 + 4) | 55.6 | 48.2 | 47.6 | 48.3 |
| $M_H$ (dN-m) (30 min) | 46.34 | 42.44 | 40.52 | 42.87 |
| $M_L$ (dN-m) | 9.12 | 8.54 | 8.40 | 9.03 |
| $M_H - M_L$ | 37.22 | 33.90 | 32.12 | 33.84 |
| T90 (min) (30 min) | 4.57 | 12.66 | 12.03 | 12.23 |
| Ts1 (min) | 2.28 | 8.32 | 8.00 | 8.02 |

TABLE 3

Physical properties of rubber compositions

| Composition No. | Comparative Example 10 | Comparative Example 11 | Example 12 | Example 13 |
|---|---|---|---|---|
| Hardness (Shore A) | 68 | 62 | 60 | 63 |
| Tensile Strength (MPa) | 30.50 | 29.18 | 30.04 | 25.91 |
| Elongation (%) | 593 | 490 | 525 | 431 |
| 25% Modulus (MPa) | 1.21 | 0.993 | 0.918 | 0.996 |
| 100% Modulus (MPa) | 3.14 | 2.36 | 2.13 | 2.44 |
| 300% Modulus (MPa) | 14.47 | 15.40 | 14.25 | 15.98 |
| RI (300%/25%) | 11.96 | 15.51 | 15.52 | 16.04 |
| RI (300%/100%) | 4.61 | 6.53 | 6.69 | 6.55 |
| Rebound (25° C.) | 50 | 58 | 60 | 57 |
| Rebound (100° C.) | 66 | 75 | 73 | 76 |

TABLE 4

Dynamic properties of rubber compositions

| Composition No. | Comparative Example 10 | Comparative Example 11 | Example 12 | Example 13 |
|---|---|---|---|---|
| $G'_{initial}$ (MPa) | 5.44 | 3.75 | 3.11 | 3.51 |
| $\Delta G'$ (MPa) | 3.28 | 1.74 | 1.39 | 1.58 |
| $G''_{max}$ (MPa) | 0.529 | 0.298 | 0.237 | 0.289 |
| $\tan \delta_{max}$ | 0.186 | 0.107 | 0.110 | 0.110 |
| $\tan \delta$ 0° C. | 0.136 | 0.147 | 0.147 | 0.15 |
| G' 0° C. (MPa) | 7.30 | 5.0 | 4.07 | 4.85 |
| G' 60° C. (MPa) | 4.78 | 3.15 | 2.65 | 2.98 |
| $\tan \delta$ 60° C. | 0.100 | 0.091 | 0.088 | 0.092 |

Examination of the data for compositions presented in Tables 2, 3 and 4 leads to the following observations: the Mooney viscosity values of Examples 12 and 13 are all low, indicating the good ability of the compositions to be processed in the uncured state and scorching times are long enough to provide a good safety margin.

Compared with the composition of comparative Example 10 (the control composition for Silquest A-1289 silane), those of Examples 12 and 13 have significantly better overall characteristics. The advantage for reinforcement power obtained with silane from Examples 12 and 13 will be readily apparent to those skilled in the art. In particular, the reinforcement indexes (300%/100%) are appreciably higher for Examples 12 and 13 than for comparative Example 10 indicating better reinforcement for the former compared with the latter.

Compared with the composition of comparative Example 11, those of Examples 12 and 13 also have good overall characteristics. However, the silanes in compositions of Examples 12 and 13 can be manufactured in much higher yield and at much lower cost. Accordingly, the compositions according to the present invention offers good overall characteristics with easy manufacturing process at low cost.

The rubber composition of this invention is particularly advantageous for use in the manufacture of tire treads exhibiting low rolling resistance and high wear resistance, especially when the treads are based on natural rubber or synthetic polyisoprene.

While the invention has been described with reference to a number of exemplary embodiments, it will be understood by those skilled in the art that various changes can be made and equivalents can be substituted for elements thereof without departing from the scope of the invention. In addition, many modifications can be made to adapt a particular situation or material to the teachings of the invention without departing from essential scope thereof. Therefore, it is intended that the invention not be limited to any particular exemplary embodiment disclosed herein.

What is claimed is:

1. A halo-containing aralkylsilane of the generalized structural Formula (1):

$$X^1X^2X^3Si\text{—}C(R^1)_{2-a}(Z^1_a)\text{-}G\text{-}(CR_{3-c}\text{—}Z^2_c)_b \quad (1)$$

wherein:
- $X^1$ is a hydrolyzable moiety selected from the group consisting of Cl—, Br—, I—, $R^2O$—, $R^2(\!=\!O)O$—, $R^2_2C\!=\!NO$—, and $R^2_2NO$—, wherein each $R^2$ is independently selected from the group consisting of hydrogen, straight, cyclic or branched alkyl, alkenyl, aryl and aralkyl groups wherein each $R^2$, other than hydrogen, contains from 1 to 18 carbon atoms and optionally at least one heteroatom selected from the group consisting of oxygen and sulfur;
- each $X^2$ and $X^3$ is independently selected from $X^1$ and $R^3$ groups wherein each $R^3$ is independently selected from the group consisting of hydrogen, alkyl, alkenyl, aryl and aralkyl groups wherein each $R^3$, other than hydrogen, contains from 1 to 18 carbon atoms and optionally at least one heteroatom selected from the group consisting of oxygen and sulfur;
- $R^1$ is selected from the group consisting of hydrogen, alkyl, alkenyl, aryl and aralkyl wherein $R^1$, other than hydrogen, contains from 1 to 10 carbon atoms, and optionally at least one heteroatom selected from the group consisting of oxygen, sulfur, fluorine, chlorine, bromine and iodine;
- each $Z^1$ and $Z^2$ is independently a halogen atom selected from the group consisting of F—, Cl—, Br— and I—;
- G is a monovalent or polyvalent aromatic hydrocarbon group of Formula (2):

$$(-)_{1+b}C_6R^4_{5-b} \quad (2)$$

wherein the six carbon atoms are part of an aromatic ring structure and each occurrence of $R^4$ is independently selected from the group consisting of hydrogen, alkyl, alkenyl, aryl and aralkyl groups wherein each $R^4$, other than hydrogen, contains from 1 to 18 carbon atoms;
- each occurrence of R is independently selected from the group consisting of hydrogen, alkyl, alkenyl, aryl and aralkyl wherein each R, other than hydrogen, contains from 1 to 30 carbon atoms; and,
- a, b and c are integers whereby a is 1; b is from 0 to 5; and c is from 1 to 3.

2. The halo-containing aralkylsilane of claim 1 wherein $X^1$ is an alkoxy group.

3. The halo-containing aralkylsilane of claim 1 wherein both $Z^1$ and $Z^2$ are halogen atom Cl.

4. The halo-containing aralkylsilane of claim 1 wherein $R^1$ is methyl, ethyl or propyl; each $R^2$ is independently methyl, ethyl or propyl; each $R^3$ is independently methyl; each $R^4$ is independently hydrogen or methyl; $X^1$ is ethoxy; each $X^2$ and $X^3$ is independently ethoxy or methyl; b is 0 or 1 and c is 1 to 3.

5. The halo-containing aralkylsilane of claim 4 wherein $R^2$ is ethyl; $X^2$ and $X^3$ are ethoxy; b is 1 and c is 1.

6. The halo-containing aralkylsilane of claim 1 selected from the group consisting of: [1-chloro-1-(4-chloromethyl-phenyl)-ethyl]-diethoxy-methyl-silane, [1-chloro-1-(4-chloromethyl-phenyl)-ethyl]-triethoxy-silane, [1-chloro-1-(4-chloromethyl-phenyl)-ethyl]-ethoxy-dimethyl-silane, [1-bromo-1-(4-bromomethyl-phenyl)-ethyl]-diethoxy-methyl-silane, [1-bromo-1-(4-bromomethyl-phenyl)-ethyl]-triethoxy-silane, [1-Chloro-1-(4-methyl-phenyl)-ethyl]-diethoxy-methyl-silane, [1-chloro-1-(4-methyl-phenyl)-ethyl]-triethoxy-silane, [1-chloro-1-(4-chloromethyl-phenyl)-propyl]-diethoxy-methyl-silane, {1-chloro-1-[4-(1-chloro-ethyl)-phenyl]-propyl}-triethoxy-silane, [1-chloro-1-(4-dichloromethyl-phenyl)-propyl]-diethoxy-methyl-silane, [1-chloro-1-(4-dichloromethyl-phenyl)-propyl]-triethoxy-silane, [1-chloro-1-(4-trichloromethyl-phenyl)-propyl]-diethoxy-methyl-silane, [1-chloro-1-(4-trichloromethyl-phenyl)-propyl]-triethoxy-silane, [1-chloro-1-(4-chloromethyl-phenyl)-ethyl]-trimethoxy-silane, [1-chloro-1-(4-chloromethyl-phenyl)-ethyl]-tripropoxy-silane, and chloro-[1-chloro-1-(4-chloromethyl-phenyl)-propyl]-dimethyl-silane.

7. A mixture comprising a partial or complete hydrolyzate of at least one halo-containing aralkylsilane of claim 1.

8. A composition comprising: (a) at least one halo-containing aralkylsilane of the structural Formula (1):

$$X^1X^2X^3Si\text{—}C(R^1)_{2-a}(Z^1_a)\text{-}G\text{-}(CR_{3-c}\text{—}Z^2_c)_b \quad (1)$$

where a is 1; and (b) at least one silane of the structural Formula (1) where a is 0,
wherein $X^1$ is a hydrolyzable moiety selected from the group consisting of Cl—, Br—, I—, $R^2O$—, $R^2(\!=\!O)O$—, $R^2_2C\!=\!NO$—, and $R^2_2NO$—, wherein each $R^2$ is independently selected from the group consisting of hydrogen, straight, cyclic or branched alkyl, alkenyl, aryl and aralkyl groups wherein each $R^2$, other than hydrogen, contains from 1 to 18 carbon atoms and optionally at least one heteroatom selected from the group consisting of oxygen and sulfur;
- each $X^2$ and $X^3$ is independently selected from $X^1$ and $R^3$ groups wherein each $R^3$ is independently selected from the group consisting of hydrogen, alkyl, alkenyl, aryl and aralkyl groups wherein each $R^3$, other than hydrogen, contains from 1 to 18 carbon atoms and optionally at least one heteroatom selected from the group consisting of oxygen and sulfur;
- each $R^1$ is independently selected from the group consisting of hydrogen, alkyl, alkenyl, aryl and aralkyl wherein each $R^1$, other than hydrogen, contains from 1 to 10 carbon atoms, and optionally at least one heteroatom selected from the group consisting of oxygen, sulfur, fluorine, chlorine, bromine and iodine;
- each $Z^1$ and $Z^2$ is independently a halogen atom selected from the group consisting of F—, Cl—, Br— and I—;
- G is a monovalent or polyvalent aromatic hydrocarbon group of Formula (2):

$$(-)_{1+b}C_6R^4_{5-b} \quad (2)$$

wherein the six carbon atoms are part of an aromatic ring structure and each occurrence of $R^4$ is independently selected from the group consisting of hydrogen, alkyl, alkenyl, aryl and aralkyl groups wherein each $R^4$, other than hydrogen, contains from 1 to 18 carbon atoms;
- each occurrence of R is independently selected from the group consisting of hydrogen, alkyl, alkenyl, aryl and aralkyl wherein each R, other than hydrogen, contains from 1 to 30 carbon atoms; and,
- b and c are integers whereby b is from 0 to 5; and c is from 1 to 3, with the proviso that a+b is equal to or greater than 1.

9. A process for preparing a halo-containing aralkylsilane comprising the steps of:
(a) reacting a hydridosilane (i) of general Formula (3):

$$HSiX^4X^5X^6 \quad (3)$$

wherein $X^4$ is a hydrolyzable moiety selected from the group consisting of F—, Cl—, Br— and I—; each $X^5$ and $X^6$ is independently selected from $X^4$ and $R^3$ groups wherein each $R^3$ is independently selected from the group consisting of hydrogen, alkyl, alkenyl, aryl and aralkyl groups wherein each $R^3$, other than hydrogen, contains from 1 to 18 carbon atoms and optionally at least one heteroatom selected from the group consisting of oxygen and sulfur;

with a carbon-carbon double bond-containing aralkane (ii) of Formula (4):

$$R^5R^6C=C(R^1)-C_6R^4_{5-b}(CR_3)_b \quad (4)$$

wherein each occurrence of R is independently selected from the group consisting of hydrogen, alkyl, alkenyl, aryl and aralkyl wherein each R, other than hydrogen, contains from 1 to 30 carbon atoms; each occurrence of $R^1$ is independently selected from the group consisting of hydrogen, alkyl, alkenyl, aryl and aralkyl wherein each $R^1$, other than hydrogen, contains from 1 to 10 carbon atoms; each occurrence of $R^4$ is independently selected from the group consisting of hydrogen, alkyl, alkenyl, aryl and aralkyl groups wherein each $R^4$, other than hydrogen, contains from 1 to 18 carbon atoms; each $R^5$ and $R^6$ is independently selected from the group consisting of hydrogen, alkyl, alkenyl, aryl or aralkyl wherein each $R^5$ and $R^6$, other than hydrogen, contains from 1 to 9 carbon atoms; and b is an integer of from 0 to 5;

in the presence of an effective amount of an alpha-selective hydrosilylation catalyst (iii) to provide an aralkylsilane of Formula (5):

$$X^4X^5X^6Si-C(R^1)_2-C_6R^4_{5-b}-(CR_3)_b \quad (5)$$

(b) reacting the reaction product of step (a) with halogen (iv), optionally in the presence of an effective amount of halogenation catalyst (v) to yield a halo-containing aralkylsilane of Formula (6):

$$X^4X^5X^6Si-C(R^1)_{2-a}(Z^1_a)-G-(CR_{3-c}-Z^2_c)_b \quad (6)$$

wherein:
each G is independently a monovalent or polyvalent aromatic hydrocarbon group of Formula (2):

$$(-)_{1+b}C_6R^4_{5-b} \quad (2)$$

wherein the six carbon atoms are part of an aromatic ring structure and each occurrence of $R^4$ is independently selected from the group consisting of hydrogen, alkyl, alkenyl, aryl and aralkyl groups wherein each $R^4$, other than hydrogen, contains from 1 to 18 carbon atoms;

each occurrence of $Z^1$ and $Z^2$ is independently a halogen atom selected from the group consisting of F—, Cl—, Br— and I—; and, a, b and c are integers whereby a is 0 or 1; b is from 0 to 5, and c is from 1 to 3, with the proviso that a+b is equal to or greater than 1; and, (c) optionally, reacting the halo-containing aralkylsilane of step (b) with $X^1$—H, wherein $X^1$ is a hydrolyzable moiety selected from the group consisting of Cl—, Br—, I—, $R^2O$—, $R^2(=O)O$—, $R^2_2C=NO$—, and $R^2_2NO$—, wherein each $R^2$ is independently selected from the group consisting of hydrogen, straight, cyclic or branched alkyl, alkenyl, aryl and aralkyl groups wherein each $R^2$, other than hydrogen, contains from 1 to 18 carbon atoms and optionally at least one heteroatom selected from the group consisting of oxygen and sulfur.

10. The process of claim 9 wherein the hydridosilane (i) is selected from the group consisting of trichlorosilane, methyldichlorosilane, dimethylchlorosilane, tribromosilane, methyldibromosilane, fluorodimethylsilane, ethyldichlorosilane, phenyldichlorosilane and isopropyldichlorosilane.

11. The process of claim 9 wherein the carbon-carbon double bond-containing aralkane (ii) is selected from the group consisting of 1-methyl-4-vinyl-benzene, 1,2-dimethyl-4-vinyl-benzene, 1-isopropenyl-4-methyl-benzene, 1-methyl-4-propenyl-benzene, 1-ethyl-4-(1-methyl-propenyl)-benzene, 1-methyl-2-vinyl-benzene, 4-dimethyl-1-vinyl-benzene and 1-methyl-4-styryl-benzene.

12. A composition comprising:
(a) at least one filler; and
(b) at least one silane of claim 1 in admixture with, or chemically bonded to, the filler of component (a).

13. The composition of claim 12 wherein the filler is at least one selected from the group consisting of silica, titanium dioxide, aluminosilicate, alumina and siliceous materials, and combinations thereof.

14. A rubber composition comprising:
(a) at least one rubber component;
(b) at least one filler;
(c) optionally, at least one activating agent; and,
(d) at least one silane of claim 1.

15. The rubber composition of claim 14 wherein the filler (b) is silane-reactive.

16. The rubber composition of claim 14 wherein component (d) is present in an amount of from about 0.2 to about 20% based on the total weight of the rubber composition.

17. A process for preparing a rubber composition comprising mixing: (a) at least one rubber component; (b) at least one filler; (c) optionally, at least one activating agent; and, (d) at least one silane of claim 1 in effective amounts.

18. The process of claim 17 wherein the effective amounts of component (a), (b) and (d) are from about 30-98%, about 2-70%, and about 0.2-2%, respectively.

19. The process of claim 17 wherein the filler (b) and the silane (d) are pre-mixed or pre-reacted prior to mixing with the rubber component (a) and optionally the activating agent (c).

20. The process of claim 17 further comprising the step of curing the rubber composition to provide a cured product.

21. An article of manufacture selected from the group consisting of tires, industrial goods, shoe soles, hoses, seals, gaskets and cable jackets, at least one component of which is the cured rubber composition of claim 14.

22. The article of claim 21, wherein the article is a tire.

* * * * *